(12) United States Patent
Fukui et al.

(10) Patent No.: US 7,935,771 B2
(45) Date of Patent: May 3, 2011

(54) POLYMER HAVING SULFONIC ACID GROUP OR SULFONIC ACID ESTER GROUP AND AMIDE GROUP, AND TONER FOR DEVELOPING ELECTROSTATIC LATENT IMAGE HAVING THE POLYMER

(75) Inventors: Tatsuki Fukui, Joyo (JP); Akiko Tominaga, Kawasaki (JP); Takashi Kenmoku, Mishima (JP); Masato Minami, Yokohama (JP); Tetsuya Yano, Tokyo (JP); Takeshi Ikeda, Shizuoka-ken (JP); Atsushi Tani, Shizuoka-ken (JP); Norikazu Fujimoto, Susono (JP)

(73) Assignee: Canon Kabushiki Kaisha, Tokyo (JP)

( * ) Notice: Subject to any disclaimer, the term of this patent is extended or adjusted under 35 U.S.C. 154(b) by 138 days.

(21) Appl. No.: 11/815,844

(22) PCT Filed: Nov. 10, 2006

(86) PCT No.: PCT/JP2006/322906
§ 371 (c)(1),
(2), (4) Date: Nov. 24, 2008

(87) PCT Pub. No.: WO2007/055414
PCT Pub. Date: May 18, 2007

(65) Prior Publication Data
US 2009/0162773 A1 Jun. 25, 2009

(30) Foreign Application Priority Data
Nov. 11, 2005 (JP) .................................. 2005-328179

(51) Int. Cl.
*C08F 128/02* (2006.01)

(52) U.S. Cl. ........ 526/256; 526/257; 526/258; 526/259; 526/260; 526/261; 526/262; 526/263; 526/264; 526/265; 526/266; 526/267; 526/268; 526/269; 526/270; 526/271; 526/272; 526/273; 526/287; 526/288; 525/326.7; 525/326.8; 525/326.9; 525/327.1; 525/327.2; 525/327.3; 525/327.4; 525/327.5; 525/327.6; 525/327.7; 525/327.8; 525/328.2; 525/329.5

(58) Field of Classification Search .............. 525/326.7, 525/326.8, 326.9, 327.1, 327.2, 327.3, 327.4, 525/327.5, 327.6, 327.7, 327.8, 328.2, 329.5; 526/256, 257, 258, 259, 260, 261, 262, 263, 526/264, 265, 266, 267, 268, 269, 270, 271, 526/272, 273, 287, 288
See application file for complete search history.

(56) References Cited

U.S. PATENT DOCUMENTS

| | | | | |
|---|---|---|---|---|
| 3,497,476 A | * | 2/1970 | Bahr et al. | 526/263 |
| 3,717,687 A | * | 2/1973 | Shanley et al. | 8/186 |
| 4,438,245 A | * | 3/1984 | Satomura | 526/286 |
| 4,490,308 A | * | 12/1984 | Fong et al. | 562/106 |
| 4,812,544 A | * | 3/1989 | Sopko et al. | 526/73 |
| 5,212,270 A | * | 5/1993 | Lal | 526/287 |
| 5,453,461 A | * | 9/1995 | Heiliger et al. | 525/54.1 |
| 5,798,199 A | | 8/1998 | Bilbrey et al. | 430/110 |
| 5,962,178 A | | 10/1999 | Cheng | 430/137 |
| 5,994,430 A | * | 11/1999 | Ding et al. | 524/80 |
| 7,252,917 B2 | | 8/2007 | Ohno et al. | 430/108.24 |
| 2005/0287463 A1 | | 12/2005 | Fukui et al. | 430/111.35 |
| 2006/0035098 A1 | | 2/2006 | Fukui et al. | 428/522 |
| 2007/0059627 A1 | | 3/2007 | Fukui et al. | 430/110.3 |
| 2007/0111125 A1 | | 5/2007 | Tominaga et al. | 430/108.1 |
| 2007/0197751 A1 | * | 8/2007 | Baugh et al. | 526/266 |
| 2007/0231729 A1 | | 10/2007 | Ohno et al. | 430/108.24 |
| 2007/0275317 A1 | | 11/2007 | Fujimoto et al. | 430/109.4 |

FOREIGN PATENT DOCUMENTS

| | | |
|---|---|---|
| EP | 1 241 531 | 9/2002 |
| GB | 1036700 | 7/1966 |
| JP | 2002-138111 | 5/2002 |

(Continued)

OTHER PUBLICATIONS

Bosman, et al., "A Modular Approach toward Functionalized Three-Dimensional Macromolecules: From Synthetic Concepts to Practical Applications", J. Am. Chem. Soc., 125, 715-728, 2003. Eisenbach, et al., "Miscibility of Rigid-Rod and Random Coil Macromolecules through Acid-Base Interactions", Macromolecules, 32, 1463-1470, 1999.

(Continued)

*Primary Examiner* — Bernard Lipman
(74) *Attorney, Agent, or Firm* — Fitzpatrick, Cella, Harper & Scinto

(57) ABSTRACT

There is provided a polymer including a unit represented by Chemical Formula (1):

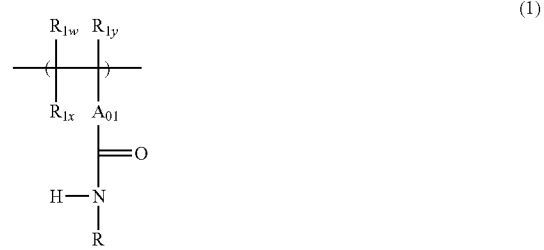

(1)

wherein R represents $-A_1-SO_2R_1$; $R_{1w}$ and $R_{1x}$ are each independently a halogen atom or a hydrogen atom; $R_{1y}$ is a $CH_3$ group, a halogen atom or a hydrogen atom; $A_{01}$ is a substituted or unsubstituted aromatic ring structure or a substituted or unsubstituted heterocyclic structure; $A_1$ is a substituted or unsubstituted aliphatic hydrocarbon structure, a substituted or unsubstituted aromatic ring structure or a substituted or unsubstituted heterocyclic structure; $R_1$ is OH, a halogen atom, ONa, OK or $OR_{1a}$; $R_{1a}$ is a substituted or unsubstituted aliphatic hydrocarbon structure, a substituted or unsubstituted aromatic ring structure or a substituted or unsubstituted heterocyclic structure.

4 Claims, 3 Drawing Sheets

FOREIGN PATENT DOCUMENTS

JP        2002-351147        12/2002

OTHER PUBLICATIONS

Ishizone, et al., "Protection and Polymerization of Functional Monomers, 22: Synthesis of Well-Defined Poly(4-Vinylbenzoic Acid) by Means of Anionic Living Polymerization of N-(4-Vinylbenzoyl)-N'-Methylpiperazine, Followed by Deprotection", Macromol. Chem. Phys., 195, 3173-3187, 1994.

Kobayashi, et al., "A New Type of Artificial Glycoconjugate Polymer: A Convenient Synthesis and Its Interaction with Lectins", Macromolecules, 30, 2016-2020, 1997.

Landry, et al., "Heats of Mixing of Strongly Interacting Model Compounds and Miscibility of the Corresponding Polymers", Macromolecules, 24, 4310-4321, 1991.

Padmapriya, et al., "A New Method for the Esterification of Sulphonic Acids", Synthetic Communications, 15(12), 1057-1062, 1985.

Tomita, et al., "Morphology of Lightly Carboxylated Polystyrene Ionomers", Macromolecules, 26, 2791-2795, 1993.

* cited by examiner

… … …

POLYMER HAVING SULFONIC ACID GROUP OR SULFONIC ACID ESTER GROUP AND AMIDE GROUP, AND TONER FOR DEVELOPING ELECTROSTATIC LATENT IMAGE HAVING THE POLYMER

This application is a National Stage Filing Under 35 U.S.C. §371 of International Application No. PCT/JP2006/322906, filed Nov. 10, 2006, which claims priority to Japanese Patent Application No. 2005-328179, filed Nov. 11, 2005. The disclosures of the prior applications are incorporated by reference herein in their entirety.

TECHNICAL FIELD

The present invention relates to a novel polymer having a sulfonic acid group or a sulfonic acid ester group and an amide group. In addition, the present invention relates to a novel compound to be used for producing the above novel polymer. Furthermore, the present invention relates to a toner for developing electrostatic latent image containing the above novel polymer.

BACKGROUND ART

A polymer having a hydrophilic group such as a sulfonic acid group is expected to be applied to various uses. And generally, a method of synthesizing a polymer containing such a sulfonic acid group is limited to a method using a specific vinyl monomer containing a sulfonic acid functional group.

Specific examples of the monomer include sulfonated styrene or AMPS (2-acrylamido-2-methylpropanesulfonic acid).

For example, Japanese Patent Application Laid-Open No. 2002-351147 discloses a copolymer of 2-acrylamido-2-methylpropane sulfonic acid salt as an example of sulfonated styrene and the other vinyl-based monomer which is copolymerizable with it.

DISCLOSURE OF INVENTION

However, it cannot be said that sulfonated styrene alone sufficiently meets the various uses mentioned above and further improvement and development of a novel polymer are demanded. An object of the present invention is to provide a novel polymer having a sulfonic acid group or a sulfonic acid ester group and an amide group as well as a method of producing it in view of the above background art. Another object of the present invention is to provide a novel compound for producing the above polymer. Still another object of the present invention is to provide a toner for developing electrostatic latent images which uses the above polymer.

Accordingly, the present inventors have conducted intensive studies aiming at developing a novel polymer to which a polar group or a hydrophilic group has been introduced and which is supposed to be useful to improve various functionalities, and consequently attained the invention described below.

The polymer of the present invention is a polymer characterized by including a unit represented by Chemical Formula (1):

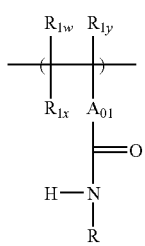

(1)

(wherein R represents $-A_1-SO_2R_1$. $R_{1w}$ and $R_{1x}$ are each independently a halogen atom or a hydrogen atom. $R_{1y}$ is a $CH_3$ group, a halogen atom or a hydrogen atom.

$A_{01}$ is a substituted or unsubstituted aromatic ring structure or a substituted or unsubstituted heterocyclic structure.

$A_1$ is a substituted or unsubstituted aliphatic hydrocarbon structure, a substituted or unsubstituted aromatic ring structure or a substituted or unsubstituted heterocyclic structure.

$R_1$ is OH, a halogen atom, ONa, OK or $OR_{1a}$. $R_{1a}$ is a substituted or unsubstituted aliphatic hydrocarbon structure, a substituted or unsubstituted aromatic ring structure or a substituted or unsubstituted heterocyclic structure).

A useful compound as a monomer for the production of the polymer of the present invention is characterized by having a structure represented by Chemical Formula (201):

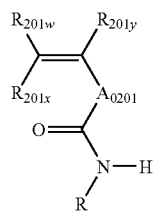

(201)

(wherein R represents $-A_{201}-SO_2R_{201}$. $R_{201w}$ and $R_{201x}$ are each independently a halogen atom or a hydrogen atom. $R_{201y}$ is a $CH_3$ group, a halogen atom or a hydrogen atom.

$A_{0201}$ is a substituted or unsubstituted aromatic ring structure or a substituted or unsubstituted heterocyclic structure.

$A_{201}$ is a substituted or unsubstituted aliphatic hydrocarbon structure, a substituted or unsubstituted aromatic ring structure or a substituted or unsubstituted heterocyclic structure.

$R_{201}$ is OH, a halogen atom, ONa, OK or $OR_{201a}$. $R_{201a}$ is a substituted or unsubstituted aliphatic hydrocarbon structure, a substituted or unsubstituted aromatic ring structure or a substituted or unsubstituted heterocyclic structure).

Another embodiment of the production process of the polymer of the present invention includes the following production process.

That is to say, it is a production process characterized by subjecting a polymer containing a unit represented by Chemical Formula (301) and at least one amine compound represented by Chemical Formula (302) to a condensation reaction to obtain a polymer containing a unit represented by Chemical Formula (1).

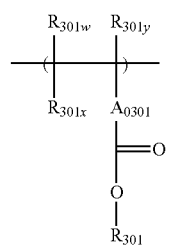

(301)

(wherein $R_{301w}$ and $R_{301x}$ are each independently a halogen atom or a hydrogen atom. $R_{301y}$ is a $CH_3$ group, a halogen atom or a hydrogen atom. $R_{301}$ is an H atom, an Na atom or a K atom).

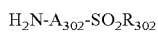

$H_2N-A_{302}-SO_2R_{302}$ (302)

(wherein $R_{302}$ is OH, a halogen atom, ONa, OK or $OR_{302a}$. $A_{302}$ and $R_{302a}$ are each independently a substituted or unsubstituted aliphatic hydrocarbon structure, a substituted or unsubstituted aromatic ring structure or a substituted or unsubstituted heterocyclic structure).

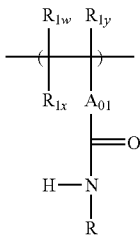

(1)

(wherein R represents -$A_1$-$SO_2R_1$. $R_{1w}$ and $R_{1x}$ are each independently a halogen atom or a hydrogen atom. $R_{1y}$ is a $CH_3$ group, a halogen atom or a hydrogen atom.

$A_{O1}$ is a substituted or unsubstituted aromatic ring structure or a substituted or unsubstituted heterocyclic structure.

$A_1$ is a substituted or unsubstituted aliphatic hydrocarbon structure, a substituted or unsubstituted aromatic ring structure or a substituted or unsubstituted heterocyclic structure.

$R_1$ is OH, a halogen atom, ONa, OK or $OR_{1a}$.

$R_{1a}$ is a substituted or unsubstituted aliphatic hydrocarbon structure, a substituted or unsubstituted aromatic ring structure or a substituted or unsubstituted heterocyclic structure).

Another embodiment of the production process of the polymer of the present invention includes a production process characterized by subjecting a polymer containing a unit represented by Chemical Formula (303) to an esterification reaction using an esterifying agent to obtain a polymer containing a unit represented by Chemical Formula (304).

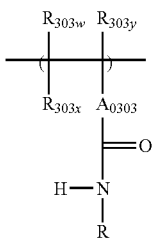

(303)

(wherein R represents -$A_{303}$-$SO_2R_{303}$. $R_{303w}$ and $R_{303x}$ are each independently a halogen atom or a hydrogen atom. $R_{303y}$ is a $CH_3$ group, a halogen atom or a hydrogen atom.

$A_{O303}$ is a substituted or unsubstituted aromatic ring structure or a substituted or unsubstituted heterocyclic structure.

$A_{303}$ is a substituted or unsubstituted aliphatic hydrocarbon structure, a substituted or unsubstituted aromatic ring structure or a substituted or unsubstituted heterocyclic structure. $R_{303}$ is OH, a halogen atom, ONa or OK).

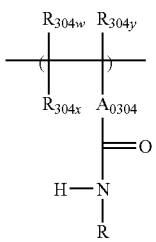

(304)

(wherein R represents -$A_{304}$-$SO_3R_{304}$. $R_{304w}$ and $R_{304s}$ are each independently a halogen atom or a hydrogen atom. $R_{304y}$ is a $CH_3$ group, a halogen atom or a hydrogen atom.

$A_{O304}$ is a substituted or unsubstituted aromatic ring structure or a substituted or unsubstituted heterocyclic structure.

$A_{304}$ is a substituted or unsubstituted aliphatic hydrocarbon structure, a substituted or unsubstituted aromatic ring structure or a substituted or unsubstituted heterocyclic structure.

$R_{304}$ is a substituted or unsubstituted aliphatic hydrocarbon structure, a substituted or unsubstituted aromatic ring structure or a substituted or unsubstituted heterocyclic structure).

The charge control agent of the present invention is a charge control agent to control the electrically charging state of fine particles, wherein the charge control agent includes at least one polymer mentioned above.

The toner for developing electrostatic latent images according to the present invention is a toner for developing electrostatic latent images characterized in that the toner for developing electrostatic latent images includes at least a binder resin, a colorant, and a polymer of the present invention mentioned above. Here, the above polymer preferably functions as a charge control agent of the toner.

According to the present invention, a novel polymer and a novel compound to produce this polymer are provided. In addition, a toner for developing electrostatic latent images using the above polymer can be provided.

BRIEF DESCRIPTION OF THE DRAWING

In FIG. 5, reference numeral 41 denotes a device for measuring the charge quantity, 42 a container for measurement, 43 a screen, 44 a lid, 45 a vacuum gauge, 46 a valve for controlling the blowing amount of air, 47 a sucking opening, 48 a condenser, and 49 an electrometer.

BEST MODE FOR CARRYING OUT THE INVENTION

Figure 1:
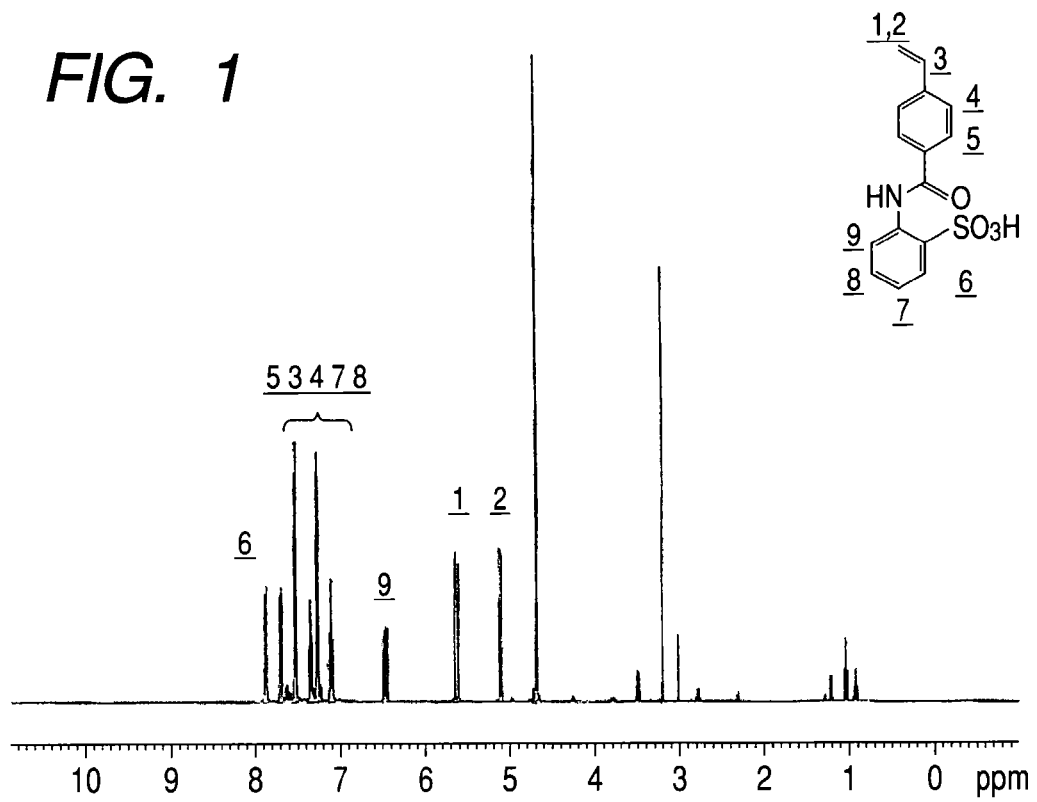
FIG. 1 is a graphical representation showing a measurement result of $^1$H-NMR in Example R-0.

Polymer and Compound of the Present Invention

The polymer of the present invention is characterized by including one or more units of the structure represented by Chemical Formula (1) mentioned above.

In the meantime, when a plurality of units are present in the polymer, each unit is represented by the definition of each formula independently from each other in the present invention. For example, there may be a plurality of the same units represented by formula (1) or there may be different units represented by formula (1). This point is also applicable to the units represented by other formulas. That is, the present invention encompasses not only cases where the above polymer is composed of the same type of unit but also cases where the above polymer is composed of different types of units.

As a unit represented by Chemical Formula (1) of a polymer of the present invention, units of Chemical Formulas (2) to (11) are preferable.

(2)

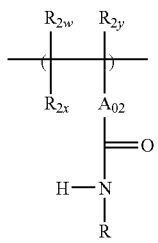

(wherein R represents -$A_2$-$SO_2R_2$. $R_{2w}$ and $R_{2x}$ are each independently a halogen atom or a hydrogen atom. $R_{2y}$ is a $CH_3$ group, a halogen atom or a hydrogen atom.

$A_{02}$ is a substituted or unsubstituted aromatic ring structure or a substituted or unsubstituted heterocyclic structure.

$A_2$ is a substituted or unsubstituted aliphatic hydrocarbon structure, a substituted or unsubstituted aromatic ring structure or a substituted or unsubstituted heterocyclic structure.

$R_2$ is OH, a halogen atom, ONa, OK or $OR_{2a}$.

$R_{2a}$ is a straight or branched alkyl group having 1 to 8 carbons or a substituted or unsubstituted phenyl group).

(3)

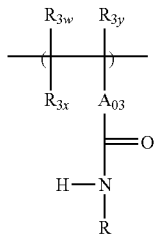

(wherein R represents -$A_3$-$SO_2R_3$. $R_{3w}$ and $R_{3x}$ are each independently a halogen atom or a hydrogen atom. $R_{3y}$ is a $CH_3$ group, a halogen atom or a hydrogen atom.

$A_{03}$ is a substituted or unsubstituted phenylene group or a substituted or unsubstituted naphthylene group.

$A_3$ is a substituted or unsubstituted aliphatic hydrocarbon structure, a substituted or unsubstituted aromatic ring structure or a substituted or unsubstituted heterocyclic structure.

$R_3$ is OH, a halogen atom, ONa, OK or $OR_{3a}$.

$R_{3a}$ is a straight or branched alkyl group having 1 to 8 carbons or a substituted or unsubstituted phenyl group).

(4)

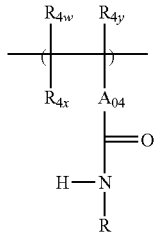

(wherein R represents -$A_4$-$SO_2R_4$. $R_{4w}$ and $R_{4x}$ are each independently a halogen atom or a hydrogen atom. $R_{4y}$ is a $CH_3$ group, a halogen atom or a hydrogen atom.

$A_{04}$ is a substituted or unsubstituted phenylene group. The substituent is at least one selected from the group consisting of a halogen atom, an alkyl group having 1 to 20 carbons, an alkoxy group having 1 to 20 carbons, an OH group, an $NH_2$ group, an $NO_2$ group, $COOR_{4g}$ ($R_{4g}$: any one of an H atom, an Na atom or a K atom), an acetamide group, an OPh group, an NHPh group, a $CF_3$ group, a $C_2F_5$ group and a $C_3F_7$ group.

$A_4$ is a straight or branched alkyl group having 1 to 8 carbons.

$R_4$ is OH, a halogen atom, ONa, OK or $OR_{4a}$.

$R_{4a}$ is a straight or branched alkyl group having 1 to 8 carbons or a substituted or unsubstituted phenyl group).

(5)

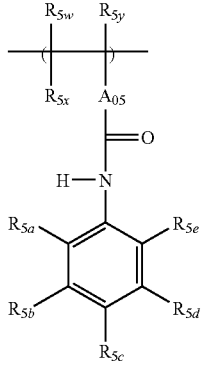

(wherein $R_{5w}$ and $R_{5x}$ are each independently a halogen atom or a hydrogen atom. $R_{5y}$ is a $CH_3$ group, a halogen atom or a hydrogen atom.

$A_{05}$ is a substituted or unsubstituted phenylene group. The substituent is at least one selected from the group consisting of a halogen atom, an alkyl group having 1 to 20 carbons, an alkoxy group having 1 to 20 carbons, an OH group, an $NH_2$ group, an $NO_2$ group, $COOR_{05g}$ ($R_{05g}$: any one of an H atom, an Na atom or a K atom), an acetamide group, an OPh group, an NHPh group, a $CF_3$ group, a $C_2F_5$ group and a $C_3F_7$ group. Ph represents a phenyl group (the same is applied to each formula).

$R_{5a}$, $R_{5b}$, $R_{5c}$, $R_{5d}$ and $R_{5e}$ are each independently $SO_2R_{5f}$ ($R_{5f}$ is OH, a halogen atom, ONa, OK or $OR_{5h}$. $R_{5h}$ represents a straight or branched alkyl group having 1 to 8 carbons or a substituted or unsubstituted phenyl group), a hydrogen atom, a halogen atom, an alkyl group having 1 to 20 carbons, an alkoxy group having 1 to 20 carbons, an OH group, an $NH_2$ group, an $NO_2$ group, $COOR_{5g}$ ($R_{5g}$: any one of an H atom, an Na atom or a K atom), an acetamide group, an OPh group, an NHPh group, a $CF_3$ group, a $C_2F_5$ group and a $C_3F_7$ group, provided that at least one of $R_{5a}$, $R_{5b}$, $R_{5c}$, $R_{5d}$ and $R_{5e}$ is $SO_2R_{5f}$).

(6a)

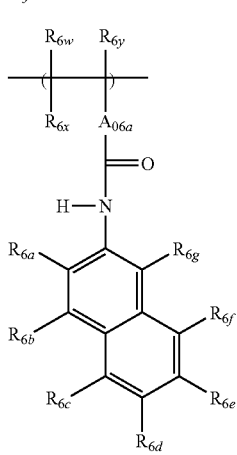

(wherein $R_{6w}$ and $R_{6x}$ are each independently a halogen atom or a hydrogen atom. $R_{6y}$ is a $CH_3$ group, a halogen atom or a hydrogen atom.

$A_{06a}$ is a substituted or unsubstituted phenylene group. The substituent is at least one selected from the group consisting of a halogen atom, an alkyl group having 1 to 20 carbons, an alkoxy group having 1 to 20 carbons, an OH group, an $NH_2$ group, an $NO_2$ group, $COOR_{06ag}$ ($R_{06ag}$: any one of an H atom, an Na atom or a K atom), an acetamide group, an OPh group, an NHPh group, a $CF_3$ group, a $C_2F_5$ group and a $C_3F_7$ group. $R_{6a}$, $R_{6b}$, $R_{6c}$, $R_{6d}$, $R_{6e}$, $R_{6f}$ and $R_{6g}$ are each independently $SO_2R_{6o}$ ($R_{6o}$ is OH, a halogen atom, ONa, OK or $OR_{6s}$. $R_{6s}$ represents a straight or branched alkyl group having 1 to 8 carbons or a substituted or unsubstituted phenyl group), a hydrogen atom, a halogen atom, an alkyl group having 1 to 20 carbons, an alkoxy group having 1 to 20 carbons, an OH group, an $NH_2$ group, an $NO_2$ group, $COOR_{6p}$ ($R_{6p}$: any one of an H atom, an Na atom or a K atom), an acetamide group, an OPh group, an NHPh group, a $CF_3$ group, a $C_2F_5$ group and a $C_3F_7$ group, provided that at least one of $R_{6a}$, $R_{6b}$, $R_{6c}$, $R_{6d}$, $R_{6e}$, $R_{6f}$ and $R_{6g}$ is $SO_2R_{6o}$).

(6b)

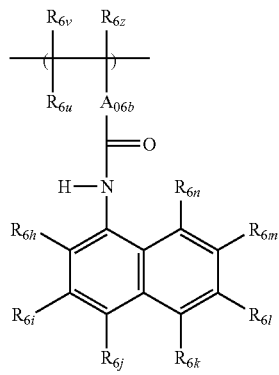

(wherein $R_{6v}$ and $R_{6u}$ are each independently a halogen atom or a hydrogen atom. $R_{6z}$ is a $CH_3$ group, a halogen atom or a hydrogen atom.

$A_{06b}$ is a substituted or unsubstituted phenylene group. The substituent is at least one selected from the group consisting of a halogen atom, an alkyl group having 1 to 20 carbons, an alkoxy group having 1 to 20 carbons, an OH group, an $NH_2$ group, an $NO_2$ group, $COOR_{06br}$ ($R_{06br}$: any one of an H atom, an Na atom or a K atom), an acetamide group, an OPh group, an NHPh group, a $CF_3$ group, a $C_2F_5$ group and a $C_3F_7$ group.

$R_{6h}$, $R_{6i}$, $R_{6j}$, $R_{6k}$, $R_{6l}$, $R_{6m}$ and $R_{6n}$ are each independently $SO_2R_{6q}$ ($R_{6q}$ is OH, a halogen atom, ONa, OK or $OR_{6t}$. $R_{6t}$ represents a straight or branched alkyl group having 1 to 8 carbons or a substituted or unsubstituted phenyl group), a hydrogen atom, a halogen atom, an alkyl group having 1 to 20 carbons, an alkoxy group having 1 to 20 carbons, an OH group, an $NH_2$ group, an $NO_2$ group, $COOR_{6r}$ ($R_{6r}$: any one of an H atom, an Na atom or a K atom), an acetamide group, an OPh group, an NHPh group, a $CF_3$ group, a $C_2F_5$ group and a $C_3F$, group, provided that at least one of $R_{6h}$, $R_{6i}$, $R_{6j}$, $R_{6k}$, $R_{6l}$, $R_{6m}$ and $R_{6n}$ is $SO_2R_{6q}$).

(7)

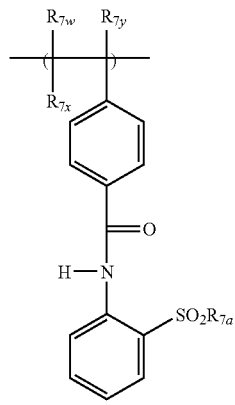

(wherein $R_{7w}$ and $R_{7x}$ are each independently a halogen atom or a hydrogen atom. $R_{7y}$ is a $CH_3$ group, a halogen atom or a hydrogen atom. $R_{7a}$ is OH, a halogen atom, ONa, OK or $OR_{7b}$.

$R_{7b}$ is a straight or branched alkyl group having 1 to 8 carbons or a substituted or unsubstituted phenyl group).

(8)

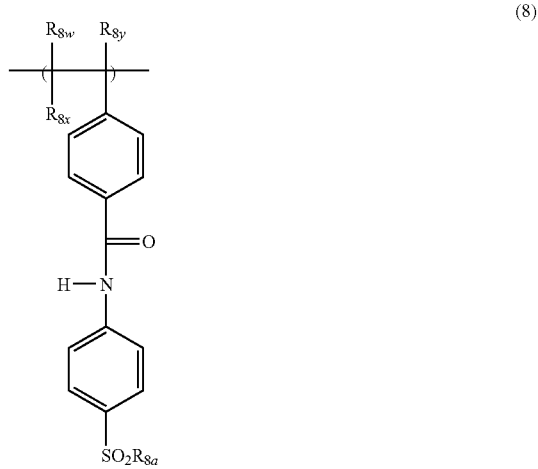

(wherein $R_{8w}$ and $R_{8x}$ are each independently a halogen atom or a hydrogen atom. $R_{8y}$ is a $CH_3$ group, a halogen atom or a hydrogen atom. $R_{8a}$ is OH, a halogen atom, ONa, OK or $OR_{8b}$.

$R_{8b}$ is a straight or branched alkyl group having 1 to 8 carbons or a substituted or unsubstituted phenyl group).

(9)

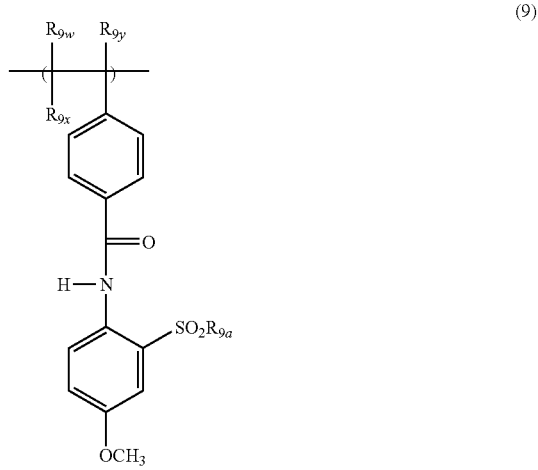

(wherein $R_{9w}$ and $R_{9x}$ are each independently a halogen atom or a hydrogen atom. $R_{9y}$ is a $CH_3$ group, a halogen atom or a hydrogen atom.

$R_{9a}$ is OH, a halogen atom, ONa, OK or $OR_{9b}$.

$R_{9b}$ is a straight or branched alkyl group having 1 to 8 carbons or a substituted or unsubstituted phenyl group).

(10)

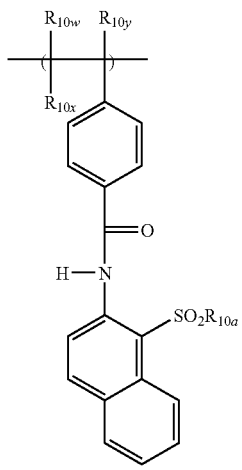

(wherein $R_{10w}$ and $R_{10x}$ are each independently a halogen atom or a hydrogen atom. $R_{10y}$ is a $CH_3$ group, a halogen atom or a hydrogen atom. $R_{10a}$ is OH, a halogen atom, ONa, OK or $OR_{10b}$.

$R_{10b}$ is a straight or branched alkyl group having 1 to 8 carbons or a substituted or unsubstituted phenyl group).

(11)

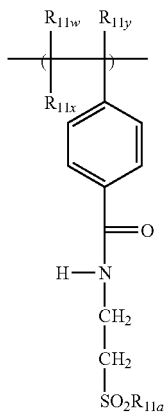

(wherein $R_{11w}$ and $R_{11x}$ are each independently a halogen atom or a hydrogen atom. $R_{11y}$ is a $CH_3$ group, a halogen atom or a hydrogen atom. $R_{11a}$ is OH, a halogen atom, ONa, OK or $OR_{11b}$.

$R_{11b}$ is a straight or branched alkyl group having 1 to 8 carbons or a substituted or unsubstituted phenyl group).

The polymer of the present invention may be a copolymer which includes at least one unit derived from a vinyl-based monomer and represented by Chemical Formula (101) in addition to any one of the units represented by Chemical Formulas (1) to (11).

(101)

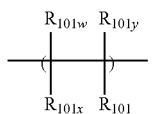

(wherein $R_{101w}$ and $R_{101x}$ are each independently a halogen atom or a hydrogen atom. $R_{101y}$ is a $CH_3$ group, a halogen atom or a hydrogen atom.

$R_{101}$ is a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{101a}$, —O—$R_{101b}$, —COO—$R_{101c}$, —OCO—$R_{101d}$, —CONR$_{101e}$R$_{101f}$, —CN or a ring structure containing an N atom. $R_{101a}$, $R_{101b}$, $R_{101c}$, $R_{101d}$, $R_{101e}$ and $R_{101f}$ are each independently a hydrogen atom, a substituted or unsubstituted aliphatic hydrocarbon structure, a substituted or unsubstituted aromatic ring structure or a substituted or unsubstituted heterocyclic structure).

Here, the ratio of the units in the copolymer having the unit represented by Chemical Formula (1) and the unit derived from a vinyl-based monomer and represented by Chemical Formula (101) in the present invention is 0.1 to 100 mol %, more preferably 1.0 to 50 mol % in terms of the content of the unit represented by Chemical Formula (1).

The molecular weight distribution (weight average molecular weight/number average molecular weight=Mw/Mn) of the polymer of the present invention can be 1<Mw/Mn<10, and preferably expressed as 1<Mw/Mn<2.

The copolymer comprising any one of the units represented by Chemical Formulas (1) to (11) and a unit derived from a vinyl-based monomer and represented by Chemical Formula (101) of the present invention can be a block copolymer. It is preferable that the number average molecular weight of a polymer of the present invention is from 1000 to 1000000.

Compounds which can be used as a monomer for the production of the polymer of the present invention include a compound having a structure represented by Chemical Formula (201).

(201)

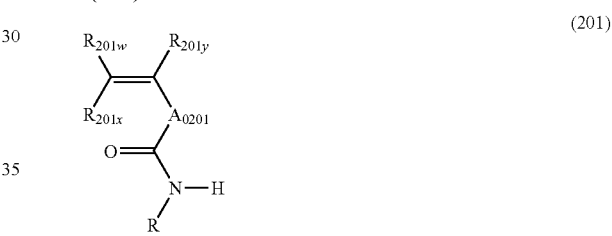

(wherein R represents -$A_{201}$-$SO_2R_{201}$. $R_{201w}$ and $R_{201x}$ are each independently a halogen atom or a hydrogen atom. $R_{201y}$ is a $CH_3$ group, a halogen atom or a hydrogen atom.

$A_{0201}$ is a substituted or unsubstituted aromatic ring structure or a substituted or unsubstituted heterocyclic structure.

$A_{201}$ is a substituted or unsubstituted aliphatic hydrocarbon structure, a substituted or unsubstituted aromatic ring structure or a substituted or unsubstituted heterocyclic structure.

$R_{201}$ is OH, a halogen atom, ONa, OK or $OR_{201a}$.

$R_{201a}$ is a substituted or unsubstituted aliphatic hydrocarbon structure, a substituted or unsubstituted aromatic ring structure or a substituted or unsubstituted heterocyclic structure).

Compounds which can be used as a monomer for the production of the polymer of the present invention include a compound having a structure represented by Chemical Formula (202).

(202)

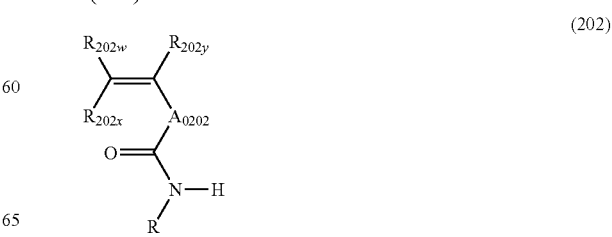

(wherein R represents -$A_{202}$-$SO_2R_{202}$. $R_{202w}$ and $R_{202x}$ are each independently a halogen atom or a hydrogen atom. $R_{202y}$ is a $CH_3$ group, a halogen atom or a hydrogen atom.

$A_{0202}$ is a substituted or unsubstituted aromatic ring structure or a substituted or unsubstituted heterocyclic structure.

$A_{202}$ is a substituted or unsubstituted aliphatic hydrocarbon structure, a substituted or unsubstituted aromatic ring structure or a substituted or unsubstituted heterocyclic structure. $R_{202}$ is OH, a halogen atom, ONa, OK or $OR_{202a}$. $R_{202a}$ is a methyl group, an ethyl group or a phenyl group).

(Production Process)

A polymer containing a unit represented by Chemical Formula (1) mentioned above can be produced by polymerizing at least one compound represented by Chemical Formula (201).

In addition, the polymer containing the unit represented by Chemical Formula (1) of the present invention can be obtained by subjecting a polymer containing a unit represented by Chemical Formula (301) and at least one amine compound represented by Chemical Formula (302) to a condensation reaction.

In a production process of the polymer containing the unit represented by this Chemical Formula (1), it is preferable to use a condensing agent to form an amide bond in the same reaction field. As the condensing agent for this purpose, phosphoric acid-based condensing agents can be used. In addition, the condensation reaction can be performed further in the presence of pyridine.

In addition, a polymer containing a unit represented by Chemical Formula (304) of the present invention can be obtained by esterifying a polymer containing a unit represented by Chemical Formula (303) using an esterifying agent.

The above esterifying agent adopted in a production process of the polymer containing the unit represented by the above Chemical Formula (304) includes trimethylsilyldiazomethane, trimethyl orthoformate, triethyl orthoformate, tributyl orthoformate or tripropyl orthoformate.

(Charge Control Agent)

The charge control agent of the present invention controls an electric charge state of fine particles and it is characterized by including a polymer having a unit with a structure represented by Chemical Formula (1).

It is further preferable that the above particulate material be a toner for developing electrostatic latent images.

Furthermore, as the unit represented by Chemical Formula (1) of the polymer constituting the charge control agent, units represented by Chemical Formulas (2) to (11) can be used.

(More Specific Production Process of Polymer of the Present Invention)

Hereinbelow, the present invention will be described in detail by way of favorable embodiments. The polymer of the present invention having each constitution mentioned above has a characteristic extremely excellent as a charge control agent. Besides, the toner for developing electrostatic latent images containing a charge control agent which uses this polymer has a remarkable effect when, above all, it is used for an image forming apparatus having a developing system by electrophotography. The following processes can be exemplified as a production process of this polymer.

For example, the polymer having the unit represented by Chemical Formula (1) is produced by reaction between the polymer having a unit represented by Chemical Formula (301) to be used as a starting material and at least one compound represented by Chemical Formula (302).

In this method, by using the polymer having the unit represented by Chemical Formula (301) and a molecular weight distribution 1<Mw/Mn<2 as a starting material, the polymer having the unit represented by Chemical Formula (1) and a molecular weight distribution which is in the above range can be synthesized.

A block copolymer including the unit represented by Chemical Formula (301) and a unit derived from a vinyl-based monomer represented by Chemical Formula (101) can be also used as a starting material. A block copolymer including the unit represented by Chemical Formula (1) and the unit derived from a vinyl-based monomer represented by Chemical Formula (101) can be synthesized in such a case.

(Production Process of Polymer Containing Unit Represented by Chemical Formula (301))

The polymer having a carboxyl group represented by Chemical Formula (301) can be produced as a copolymer having the vinyl-based monomer unit represented by Chemical Formula (101) in addition to the unit of Chemical Formula (301) using a well-known polymerization method and a polymer reaction.

As the vinyl-based monomer for introducing the unit represented by Chemical Formula (101) each of the following compounds can be mentioned.

Styrene and derivatives thereof, ethylenically unsaturated monoolefines, vinyl halides, vinyl esters α-methylene aliphatic monocarboxylic acid esters, vinyl ethers, acrylic acid or methacryl acid derivatives.

A polymer having a vinylbenzoic acid unit can be obtained as follows.

As for the polymer having a carboxyl group represented by Chemical Formula (301), a protecting group is introduced into the carboxylic acid of vinylbenzoic acid to synthesize a monomer and after it is polymerized, the protecting group is removed by performing a polymer reaction to obtain a polymer having a vinylbenzoic acid unit.

The polymer having the unit represented by Chemical Formula (301) and a molecular weight distribution 1.00<Mw/Mn<2.00 can be synthesized by using a living polymerization method.

As living radical polymerization, for example, atom transfer radical polymerization and nitroxide mediated polymerization are explained below.

First, the case where the living radical polymerization is atom transfer radical polymerization is explained.

According to atom transfer radical polymerization, a polymer of a narrow molecular weight distribution can be obtained through a fast transfer reaction at the end of polymer chains, for example, by using a copper halide-bipyridyl complex.

As a reaction solvent, for example, dimethylsulfoxide, dimethylformamide, etc. can be used.

Next, the case where the living radical polymerization is nitroxide mediated polymerization is explained.

2,2,6,6-tetramethylpiperidine (TEMPO) which is one of nitroxyl radicals and in which unpaired electrons are delocalized is hard to be bonded to a radical which gives low dissociation energy when bonded. Using this property, a polymer having a narrow molecular weight distribution by nitroxide mediated polymerization using a nitroxyl radical with benzoyl peroxide (BPO) and azobisisobutyronitrile (AIBN) as an initiator.

A polymerizable monomer, an initiator and a nitroxyl radical are added to the reaction solvent, the reaction system is substituted with an inert gas and nitroxide mediated polymerization is performed.

As for the nitroxyl radical, those described below, for example, can be used.

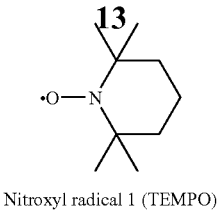

Nitroxyl radical 1 (TEMPO)

As for the reaction solvent, dimethylsulfoxide, dimethylformamide, etc., for example, can be used.

The block copolymer including the unit represented by Chemical Formula (301) and the unit derived from a vinyl-based monomer represented by Chemical Formula (101) can be synthesized by using a living polymerization method among well-known polymerization methods. Among living polymerization methods, living radical polymerization in particular is relatively easy.

Specifically, after having formed a homopolymer with a structure represented by Chemical Formula (301) by living radical polymerization, a polymer having a structure represented by Chemical Formula (101) is copolymerized to one end of the homopolymer by living radical polymerization. A precursor of the target block copolymer can be obtained in this way.

The order for forming the block copolymer may be opposite.

This living radical polymerization, preferably atom transfer radical polymerization and nitroxide mediated polymerization can be performed in the same way as in the case of the polymer having the unit of Chemical Formula (301) mentioned above.

(Compound Represented by Chemical Formula (302))

The compound represented by Chemical Formula (302) to be used in the present invention may be a compound in which $A_{302}$ is as follows.

That is, such compound may be a compound in which $A_{302}$ is a straight or branched alkylene group having 1 to 8 carbons, a substituted or unsubstituted phenyl group, a substituted or unsubstituted naphthyl group, or a substituted or unsubstituted heterocyclic structure containing any one or more of N, S and O.

When $A_{302}$ is a ring structure, unsubstituted rings may be further condensed with it.

Specific examples of the compound where $A_{302}$ is a straight or branched alkylene group having 1 to 8 carbons include the following. That is to say, 2-aminoethanesulfonic acid (taurine), 3-aminopropanesulfonic acid, 4-aminobutane sulfonic acid, 2-amino-2-methylpropanesulfonic acid and alkali metal salts thereof.

The compound where $A_{302}$ is a substituted or unsubstituted phenyl group is represented by Chemical Formula (26).

(26)

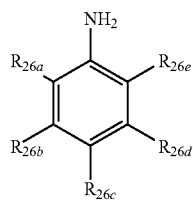

(wherein $R_{26a}$, $R_{26b}$, $R_{26c}$, $R_{26d}$ and $R_{26e}$ each independently represents $SO_2R_{26f}$ ($R_{26f}$ is OH, a halogen atom, ONa, OK or $OR_{26h}$. $R_{26h}$ represents a substituted or unsubstituted aliphatic hydrocarbon structure, a substituted or unsubstituted aromatic ring structure or a substituted or unsubstituted heterocyclic structure), a hydrogen atom, a halogen atom, an alkyl group having 1 to 20 carbons, an alkoxy group having 1 to 20 carbons, an OH group, an $NH_2$ group, an $NO_2$ group, $COOR_{26g}$ ($R_{26g}$ represents any one of an H atom, an Na atom and a K atom), an acetamide group, an OPh group, an NHPh group, a $CF_3$ group, a $C_2F_5$ group or a $C_3F_7$ group and wherein at least one of $R_{26a}$, $R_{26b}$, $R_{26c}$, $R_{26d}$ and $R_{26e}$ is $SO_2R_{26f}$).

The compound represented by Chemical Formula (26) includes various aminobenzenesulfonic acid derivatives and salts thereof such as p-aminobenzenesulfonic acid (sulfanilic acid). Besides, it also includes esterified compounds such as methyl ester compounds or phenyl ester compounds of various aminobenzenesulfonic acid derivatives such as 2-aminobenzenesulfonic acid methyl ester.

The compound where $A_{27}$ is a substituted or unsubstituted naphthyl group is represented by Chemical Formulas (27a) and (27b).

(27a)

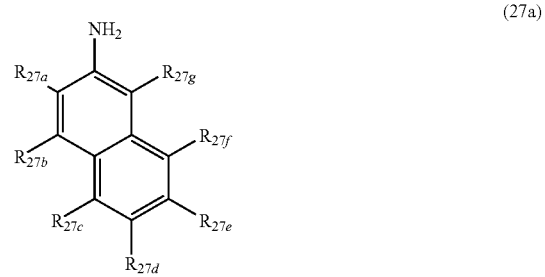

(wherein $R_{27a}$, $R_{27b}$, $R_{27c}$, $R_{27d}$, $R_{27e}$, $R_{27f}$ and $R_{27g}$ each independently represents $SO_2R_{27o}$ ($R_{27o}$ is OH, a halogen atom, ONa, OK or $OR_{27s}$. $R_{27s}$ represents a substituted or unsubstituted aliphatic hydrocarbon structure, a substituted or unsubstituted aromatic ring structure or a substituted or unsubstituted heterocyclic structure), a hydrogen atom, a halogen atom, an alkyl group having 1 to 20 carbons, alkoxy group having 1 to 20 carbons, an OH group, an $NH_2$ group, an $NO_2$ group, $COOR_{27p}$ ($R_{27p}$ represents any one of an H atom, an Na atom and a K atom), an acetamide group, an OPh group, an NHPh group, a $CF_3$ group, a $C_2F_5$ group or a $C_3F_7$ group and wherein at least one of $R_{27a}$, $R_{27b}$, $R_{27c}$, $R_{27d}$, $R_{27e}$, $R_{27f}$ and $R_{27g}$ is each independently $SO_2R_{27o}$).

(27b)

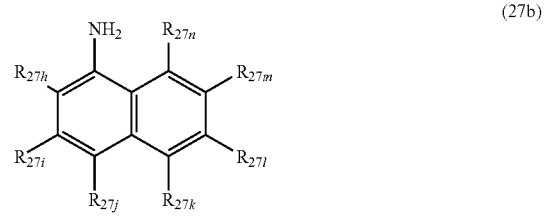

(wherein $R_{27h}$, $R_{27i}$, $R_{27j}$, $R_{27k}$, $R_{27l}$, $R_{27m}$ and $R_{27n}$ each independently represents $SO_2R_{27q}$ ($R_{27q}$ is OH, a halogen atom, ONa, OK or $OR_{27r}$. $R_{27r}$ represents a substituted or unsubstituted aliphatic hydrocarbon structure, a substituted or unsubstituted aromatic ring structure or a substituted or unsubstituted heterocyclic structure), a hydrogen atom, a halogen atom, an alkyl group having 1 to 20 carbons, an alkoxy group having 1 to 20 carbons, an OH group, an $NH_2$ group, an $NO_2$ group, $COOR_{27r}$ ($R_{27r}$ represents any one of an H atom, an Na atom and a K atom), an acetamide group, an OPh group, an NHPh group, a $CF_3$ group, a $C_2F_5$ group or a $C_3F_7$ group and wherein at least one of $R_{27h}$, $R_{27i}$, $R_{27j}$, $R_{27k}$, $R_{27l}$, $R_{27m}$ and $R_{27n}$ is $SO_2R_{27q}$).

The compound represented by Chemical Formula (27a) or (27b) includes various naphthylamine sulfonic acid derivatives and salts thereof such as 1-naphthylamine-4-sulfonic acid. Besides, it also includes esterified compounds such as methyl ester compounds or phenyl ester compounds of various naphthylamine sulfonic acid derivatives such as 1-naphthylamine-8-sulfonic acid methyl ester.

The compound where $A_{302}$ is a substituted or unsubstituted heterocycle structure containing one or more of N, S and O includes a pyridine ring, a piperazine ring, a furan ring and a thiol ring.

(Production Process of Polymer Having One or More Units Represented by Chemical Formula (1) in a Molecule)

The condensation reaction between a polymer containing a unit represented by Chemical Formula (301) and an aminosulfonic acid compound represented by Chemical Formula (302) in the present invention is described in detail.

As for the condensation reaction between a carboxyl group and an amino group, any method such as a method using a condensing agent, a method of forming a salt and performing condensation by dehydration reaction and a method using a dehydrating agent can be employed.

The method using a condensing agent is described in detail as a production process of the present invention. As the condensing agent, phosphoric acid-based condensing agents can be used. In the reaction of the present invention, it is preferable to use a phosphate-based condensing agent. As phosphites used for this purpose, triphenyl phosphite is preferably used. The amount of the condensing agent to be used is in the range of 0.1 mol or more, preferably equal mol or more per mol of the compound represented by Chemical Formula (302). The condensing agent itself can also be used as a reaction solvent.

The amount of the compound represented by Chemical Formula (302) to be used in this method is in the range of 0.1 to 50.0 mol, preferably 1.0 to 20.0 mol per mol of the unit represented by Chemical Formula (301) to be used as a starting material. In the reaction of the present invention, a solvent can be used, if necessary. Pyridine is suitable as a solvent to be used.

In the process of the present invention, for example, the reaction time is in the range of 1 to 48 hours. The reaction liquid containing a polymer having one or more units represented by Chemical Formula (1) in a molecule and generated in this way can be removed by distillation which is a conventional method.

The reaction liquid is mixed with a solvent which is homogeneously soluble to the reaction liquid and insoluble to the polymer having one or more units represented by Chemical Formula (1) in a molecule using a solvent such as ether. Then, the polymer having one or more units represented by Chemical Formula (1) in a molecule is allowed to be reprecipitated and can be collected.

The polymer having one or more units represented by Chemical Formula (1) in a molecule thus obtained can be isolated and purified, if needed. There is no particular limitation on this isolation and purification method, and a method of using a solvent insoluble to the polymer having one or more units represented by Chemical Formula (1) in a molecule to reprecipitate the polymer and a method of using column chromatography can be used.

When the polymer having the unit represented by Chemical Formula (301) in which a molecular weight distribution is 1.00<Mw/Mn<2.00 is used as a starting material, a condensation reaction can be performed by the same method.

The condensation reaction can be also performed by the same method when the block copolymer comprising the unit represented by Chemical Formula (301) and the unit derived from a vinyl-based monomer represented by Chemical Formula (101) are used as a starting material.

It can be also synthesized by performing copolymerization using a compound represented by Chemical Formula (201), another polymerizable monomer and a polymerization initiator.

(Production Process of Compound Represented by Chemical Formula (201))

The compound represented by Chemical Formula (201) can be produced by the following method.

The synthesizing method of the compound represented by Chemical Formula (201) in the present invention is described in detail. It is synthesized by a condensation reaction of a polymerizable monomer having a carboxyl group such as vinylbenzoic acid, an acid chloride polymerizable monomer in which the carboxyl group is converted to an acid chloride with various kinds of compounds having an amino group expressed by Chemical Formula (401) described later.

As for the condensation reaction between a carboxyl group and an amino group, any method such as a method using a condensing agent, a method of forming a salt and performing condensation by dehydration reaction and a method using a dehydrating agent and a method of converting a carboxyl group to an acid chloride and reacting it with an amino group can be employed.

The method of converting a carboxyl group to an acid chloride and reacting it with an amino group is described in detail as a production process of the present invention.

Conversion of a polymerizable monomer represented by Chemical Formula (203) to an acid chloride can be performed by using a thionyl chloride which is a conventional method.

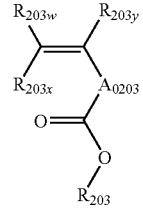

(203)

(wherein $R_{203w}$ and $R_{203x}$ are each independently a halogen atom or a hydrogen atom. $R_{203y}$ is a $CH_3$ group, a halogen atom or a hydrogen atom.

$A_{0203}$ is any one of a substituted or unsubstituted aromatic ring structure or a substituted or unsubstituted heterocycle structure. $R_{203}$ is an H atom, an Na atom or a K atom).

The amount of thionyl chloride to be used is in the range of 0.1 to 50.0 mol, preferably 1.0 to 20.0 mol per mol of the compound represented by Chemical Formula (203). Thionyl chloride itself can also be used as a reaction solvent.

The amount of the compound represented by Chemical Formula (401) described later to be used in this method is in the range of 0.1 to 50.0 mol, preferably 1.0 to 20.0 mol per mol of the unit represented by Chemical Formula (203) to be used as a starting material. In the reaction of the present invention, a solvent can be used if necessary. The solvent to be used includes dichloromethane, chloroform, carbon tetrachloride, dichloroethane, trichloroethane, etc. In this method, the reaction temperature is not limited in particular, but it is usually a temperature in the range of −30° C. to the boiling point of the solvent. It is preferable, however, to perform the reaction at an optimum temperature most suitable for the compound represented by Chemical Formula (401) described later and the reaction solvent. In the process of the present invention, the reaction time is not limited in general but usually in the range of 1 to 48 hours. The reaction liquid containing the compound represented by Chemical Formula (201) thus generated can be removed by distillation which is a conventional method.

The compound represented by Chemical Formula (201) thus obtained can be isolated and purified if needed. There is no particular limitation on this isolation and purification method, and a method using a solvent poorly soluble to the compound represented by Chemical Formula (201) to recrystallize and a method by column chromatography can be used.

Among the compounds represented by Chemical Formula (201), a compound which does not have a sulfonic acid ester unit can be synthesized by the above method.

For example, when a compound in which $R_{201}$ is OH, a halogen atom, ONa, OK is synthesized, a compound represented by Chemical Formula (201) having a sulfonic acid ester unit in which $R_{201}$ is represented by $OR_{201a}$ can be synthesized by further using an esterifying agent. The esterifying agent includes trimethylsilyldiazomethane, trimethyl orthoformate, triethyl orthoformate, etc.

In this reaction, the solvents previously explained can be used if necessary.

The amount of the esterifying agent to be used is in the range of 0.1 to 50 mol, preferably 1 to 20 mol per mol of the unit represented by Chemical Formula (201) in which $R_{201}$ is OH, a halogen atom, ONa, OK.

In this method, the reaction temperature is not limited in particular, but it is usually a temperature in the range of −20° C. to 200° C. The reaction time is not limited in general but usually in the range of 1 to 48 hours.

The reaction liquid thus generated containing the compound represented by Chemical Formula (201) which has a sulfonic acid ester unit in which $R_{201}$ represents $OR_{201a}$ can be removed by distillation which is a conventional method.

The compound thus obtained and represented by Chemical Formula (201) having a sulfonic acid ester unit in which $R_{201}$ is represented by $OR_{201a}$ can be isolated and purified if needed. There is no particular limitation on this isolation and purification method, and a method using a solvent poorly soluble to the compound which has a sulfonic acid ester unit and in which $R_{201}$ is represented by $OR_{201a}$ in Chemical Formula (201) to recrystallize and a method by column chromatography can be used.

(Compound Represented by Chemical Formula (401))

$$H_2N\text{-}A_{401}\text{-}SO_2R_{401} \quad (401)$$

(wherein $R_{401}$ is OH, a halogen atom, ONa, OK or $OR_{401a}$. $R_{401a}$ is each independently a substituted or unsubstituted aliphatic hydrocarbon structure, a substituted or unsubstituted aromatic ring structure or a substituted or unsubstituted heterocyclic structure).

The compound represented by Chemical Formula (401) to be used in the present invention is preferably the following.

That is to say, a compound in which $A_{401}$ is a straight or branched alkylene group having 1 to 8 carbons, a substituted or unsubstituted phenyl group, a substituted or unsubstituted naphthyl group, or a substituted or unsubstituted heterocycle structure containing one or more of N, S, O. When $A_{401}$ is a ring structure, an unsubstituted ring may be further condensed.

When $A_{401}$ is a straight or branched alkylene group having 1 to 8 carbons, examples of the compounds include the following. That is, 2-aminoethanesulfonic acid (taurine), 3-aminopropanesulfonic acid, 4-aminobutanesulfonic acid, 2-amino-2-methylpropanesulfonic acid, and alkali metal salts thereof.

When $A_{401}$ is a substituted or unsubstituted phenyl group, it is represented by Chemical Formula (26) explained above.

When $A_{401}$ is a substituted or unsubstituted naphthyl group, it is represented by Chemical Formula (27a) or (27b) explained above.

When $A_{401}$ is a substituted or unsubstituted heterocycle structure containing one or more of N, S, O, it includes pyridine ring, piperazine ring, furan ring, and thiol ring.

(Polymerization Method of Compound Expressed by Chemical Formula (201))

As a polymerization method of the compound represented by Chemical Formula (201), various kinds of well-known polymerization reactions can be used. Copolymerization of the compound with well-known monomers can be also performed.

Examples of monomers which can be copolymerized include styrene, o-methylstyrene.

When a compound which does not have a sulfonic acid ester unit in Chemical Formula (201) (for example, compounds in which $R_{617}$ is OH, a halogen atom, ONA, OK) is polymerized, radical polymerization in which control of polymerization conditions is relatively easy can be used.

In the meantime, when a compound has a sulfonic acid ester unit, ionic polymerization can be used.

When radical polymerization is used, the initiator includes, for example, 2,2'-azobisisobutyronitrile. In addition, water-soluble initiators such as potassium persulfate, ammonium persulfate can be also used.

These can be used alone or in combination. The amount of thereof to be used is preferably in the range of 0.0001 to 0.5 mol per mol of the total polymerizable monomers but can be appropriately determined depending on the kind of a monomer to be used, a monomer to be used for copolymerization, an initiator to be used.

In the polymerization reaction of the present invention, previously explained solvents, toluene and N,N-dimethylformamide can be used if necessary.

In addition, the polymer having the unit represented by Chemical Formula (1) in which a molecular weight distribution is $1.00<Mw/Mn<2.00$ can be synthesized by using living polymerization method in particular among well-known polymerization methods. Among the living polymerization method, living radical polymerization is relatively easy. This living radical polymerization, preferably atom transfer radical polymerization and nitroxide mediated polymerization can be performed in the same way as in the case of the polymer having the unit of Chemical Formula (301) described above.

The block copolymer including the unit represented by Chemical Formula (1) and the unit derived from a vinyl-based monomer expressed by Chemical Formula (101) can be also synthesized by using living polymerization method in particular among well-known polymerization methods.

Among the living polymerization method, living radical polymerization is relatively easy.

Specifically, after having formed a homopolymer with a structure represented by Chemical Formula (301) by living radical polymerization, a polymer having a structure represented by Chemical Formula (101) is copolymerized to one end of the homopolymer by living radical polymerization. A precursor of the target block copolymer can be obtained in this way.

The order for forming the block copolymer may be opposite. This living radical polymerization can be also performed in the same way as in the case of the polymer having the unit of Chemical Formula (301) described above.

A solvent in the reaction liquid containing the polymer of the present invention thus generated can be removed by distillation which is a conventional method. Alternatively, a solvent to which the polymer of the present invention insoluble is, for example, water, alcohols such as methanol and ethanol, or ethers is mixed with the reaction liquid homogeneously and the polymer of the present invention to be aimed at is allowed to precipitate. And the precipitation can be collected. The ethers include, for example, dimethyl ether, diethyl ether, tetrahydrofuran.

The polymer of the present invention thus obtained can be isolated and purified if needed. There is no particular limitation on this isolation and purification method, and a method using a solvent poorly soluble to the polymer of the present invention to precipitate and a method by column chromatography can be used.

(Production Process of Polymer Having One or More Units represented by Chemical Formula (304) in a Molecule)

When $R_1$ in Chemical Formula (303) is OH, a halogen atom, ONa, or OK, a polymer represented by Chemical Formula (304) in which R is represented by -$A_{304}$-$SO_3R_{304}$ can be synthesized by using an esterifying agent. For example, the esterifying agent is trimethylsilyldiazomethane, trimethyl orthoformate, triethyl orthoformate.

This reaction is described in detail below.

In this reaction, solvents described above or below can be used, if necessary. Preferably chloroform, methanol are used. The amount of the solvent to be used can be determined appropriately depending on a starting material, reaction conditions, etc.

The amount of the esterifying agent to be used is in the range of 0.1 to 50 mol, preferably 1 to 20 mol per mol of the unit represented by Chemical Formula (303).

In this method, the reaction temperature is not limited in particular, but it is usually a temperature in the range of −20° C. to 200° C. The reaction time is not limited in general but usually in the range of 1 to 48 hours.

A solvent in the reaction liquid containing the polymer of the present invention thus generated can be removed by distillation which is a conventional method.

(Application to Toner)

Use of the polymer of the present invention includes application to a toner for developing electrostatic latent images and an image forming process using it.

Specifically, it can be used as a charge control agent internally or externally added to the toner. In other words, the present invention is directed to a charge control agent containing the polymer mentioned above, and besides a toner for developing electrostatic latent images containing the charge control agent.

As a charge control agent to be used for a toner composition for developing electrostatic latent images, a charge control agent excellent in electrostatic characteristics, dispersibility of the compound in the toner resin and spendability can be provided by using, for example, a polymer compound represented by Chemical Formula (1).

In addition, the use of the polymer of the present invention enables to provide a toner for developing electrostatic latent images which reduces the fog of the image at the output of an image forming apparatus and exhibits excellent transfer property.

Furthermore, the charge control agent of the present invention can be made colorless or weakly tinted with color, and therefore, any colorant can be selected corresponding to the hue demanded for a color toner without being affected by the charge control agent. Colorless or weakly tinted charge control agent hardly obstructs the original hue which a dye or a pigment has and is preferable.

<Use as Charge Control Agent>

When the polymer of the present invention is used as a charge control agent, it is preferable that the side chain has a structure containing a sulfonic acid group or derivatives thereof like a monomer unit represented by the above Chemical Formula (1). The existence of a unit having an anionic or electron-withdrawing functional group shows excellent negative charging property.

The polymer of the present invention has a good compatibility with a binder resin of toner and in particular has an extremely good compatibility with a polyester binder resin.

Since a toner containing the polymer of the present invention has a high specific charge quantity and a good stability with the elapse of time, it stably gives a sharp image in image formation of electrostatic recording even after the toner is stored for a long time. In addition, it is colorless or weakly tinted and has a good negative charging property, it can be made into any of a black negative chargeable toner and color toner. Furthermore, wide control of compatibility is possible by appropriately selecting a type/composition ratio of the monomer unit which constitutes the polymer of the present invention.

When a resin composition is selected so that the charge control agent has a micro-phase separation structure in the toner binder, electric continuity of the toner is prohibited and an electric charge can be stably maintained.

(Addition of Polymer of the Present Invention to Toner)

The method to allow the toner to contain the charge control agent including the polymer mentioned above in the present invention includes a method in which it is internally added to the toner and a method in which it is externally added to the toner. The addition amount of the charge control agent in the case of internal addition is usually in the range of 0.1 to 50 mass %, preferably 0.2 to 20 mass % for the total mass of the toner binder and the charge control agent. The degree of improvement in charging property of the toner may not be remarkably observed when it is less than 0.1 mass %. On the other hand, there is an unfavorable case from an economic point of view when it surpasses 50 mass %. As for the mass ratio of the toner binder and the charge control agent in the case of external addition, the addition amount of the charge control agent is preferably in the range of 0.01 to 5 mass % for the total mass of the toner binder and the charge control agent, and it is particularly preferable that the charge control agent be mechnochemically adhered on the toner surface.

The molecular weight of the polymer of the present invention was measured by GPC (gel permeation chromatography). It is preferable in the present invention to use the above polymer in which the ratio (Mw/Mn) of weight average molecular weight (Mw) to number average molecular weight (Mn) measured as above is in the range of 1 to 10 when it is used as a charge control agent.

For the purpose of lowering the particle size of a discontinuous domain which the polymer of the present invention forms, a polymer which has compatibility to the polymer of the present invention and has compatibility to the toner binder may be contained as a compatibilization agent. The compatibilization agent includes the following.

For example, it is a polymer in which a polymer chain containing 50 mol % or more of a monomer having substantially the same structure as of a monomer which constitutes the polymer of the present invention and a polymer chain containing 50 mol % or more of a monomer having substantially the same structure as of a monomer which constitutes the toner binder are bonded.

As for the form of bonding, they can be connected in the form of graft or blocks.

The amount of the compatibilization agent to be used is usually 30 mass % or less, and preferably it is 1 to 10 mass % on a basis of the polymer of the present invention.

Common thermoplastic resin can be used for the toner of the present invention as a binder resin. Examples thereof include polystyrene.

When a binder resin to be used in combination with the charge control agent of the present invention is formed, cross-linking agents given below can be used if necessary. Examples of a bifunctional crosslinker include divinylbenzene.

When a binder resin to be used in combination with a charge control agent of the present invention is formed, polymerization initiators given below can be used if necessary. Examples thereof include t-butylperoxyl-2-ethyl hexanoate.

The conventionally used charge control agents other than the charge control agent of the present invention can be used in combination with the charge control agent of the present invention.

As a colorant constituting the toner for developing electrostatic latent images according to the present invention, any colorant can be used as long as it is usually used for producing toners and it is not limited in particular. Furthermore, it is preferable that a dye and a pigment be used in combination to improve the purity from a viewpoint of quality of a full color image. Usually, for obtaining the best toner characteristics, in other words, in consideration of coloring power upon printing, shape stability of a toner, scattering of a toner, the colorant is used in a ratio of 0.1 to 60 parts by mass, preferably 0.5 to 20 parts by mass for 100 parts by mass of the binder resin.

The toner for developing electrostatic latent image according to the present invention may contain the following compounds in the range which does not adversely affect the effects of the present invention in addition to the binder resin and the colorant ingredient mentioned above. For example, it is silicone resin.

Any method conventionally known can be used as a specific method for preparing the toner for developing electrostatic latent images according to the present invention having constitution as above.

In the present invention, it is preferable to externally add silica fine powder to a toner made by such a method as above in order to improve stability, developing characteristics, fluidity and durability.

In addition, it is preferable to add inorganic powders given below in order to improve the developing characteristics and the durability of the toner. For example, it is preferable to use fine powders of zinc oxide, aluminium oxide, cobalt oxide, manganese dioxide, strontium titanate and magnesium titanate. Furthermore, slippering additive powder such as Teflon may be added to the toner.

<About Carrier>

The toner for developing electrostatic latent image according to the present invention can be applied to various kinds of conventionally known toners. For example, the toner for developing electrostatic latent images by itself can be used as a developer for nonmagnetic one-component toner. The toner for developing electrostatic latent images according to the present invention can be used as a nonmagnetic toner constituting magnetic two-component developer with a magnetic carrier or a magnetic toner which is independently used as a toner for magnetic one-component toner.

<Magnetic Toner>

The toner for developing electrostatic latent images according to the present invention can be made as a magnetic toner by allowing a magnetic material to contain in toner particles. In this case, the magnetic material can also serve as a colorant. As for the magnetic materials which can be used in the present invention, the average particle diameter is preferably 2 μm or less and more preferably about 0.1 to 0.5 μm. The amount to be contained in the toner is preferably 20 to 200 parts by mass for 100 parts by mass of the binder resin, and more preferably 40 to 150 parts by mass for 100 parts by mass of the binder resin.

Furthermore, it is necessary to enable to develop minuter latent image dots faithfully to achieve high-resolution, and therefore, for example, it is preferable that a weight average diameter of the toner particle for developing electrostatic latent images according to the present invention be adjusted so that it may be in the range of 4 μm to 9 μm. Toner particles having a weight average diameter is less than 4 μm cause decrease in transfer efficiency and tend to leave much untransferred toner on the photoreceptor, which cause ununiform irregularities of the image based on fog and transfer defectiveness and that is to say unpreferable. In the meantime, when the weight average diameter of a toner particle is more than 9 μm, scattering of letters and line images tend to occur.

In the present invention, Coulter counter TA-II type or Coulter multi-sizers (manufactured by Beckman Coulter Corporation) was used for the average particle diameter of a toner and particle size distribution.

In addition, the toner for developing electrostatic latent images according to the present invention has preferably charge per unit mass (two-component method) in the range of −10 to −80 μC/g, more preferably −15 to −70 μC/g since it can improve transfer efficiency in the transfer method using a transfer member to which the voltage is applied.

Figure 5:
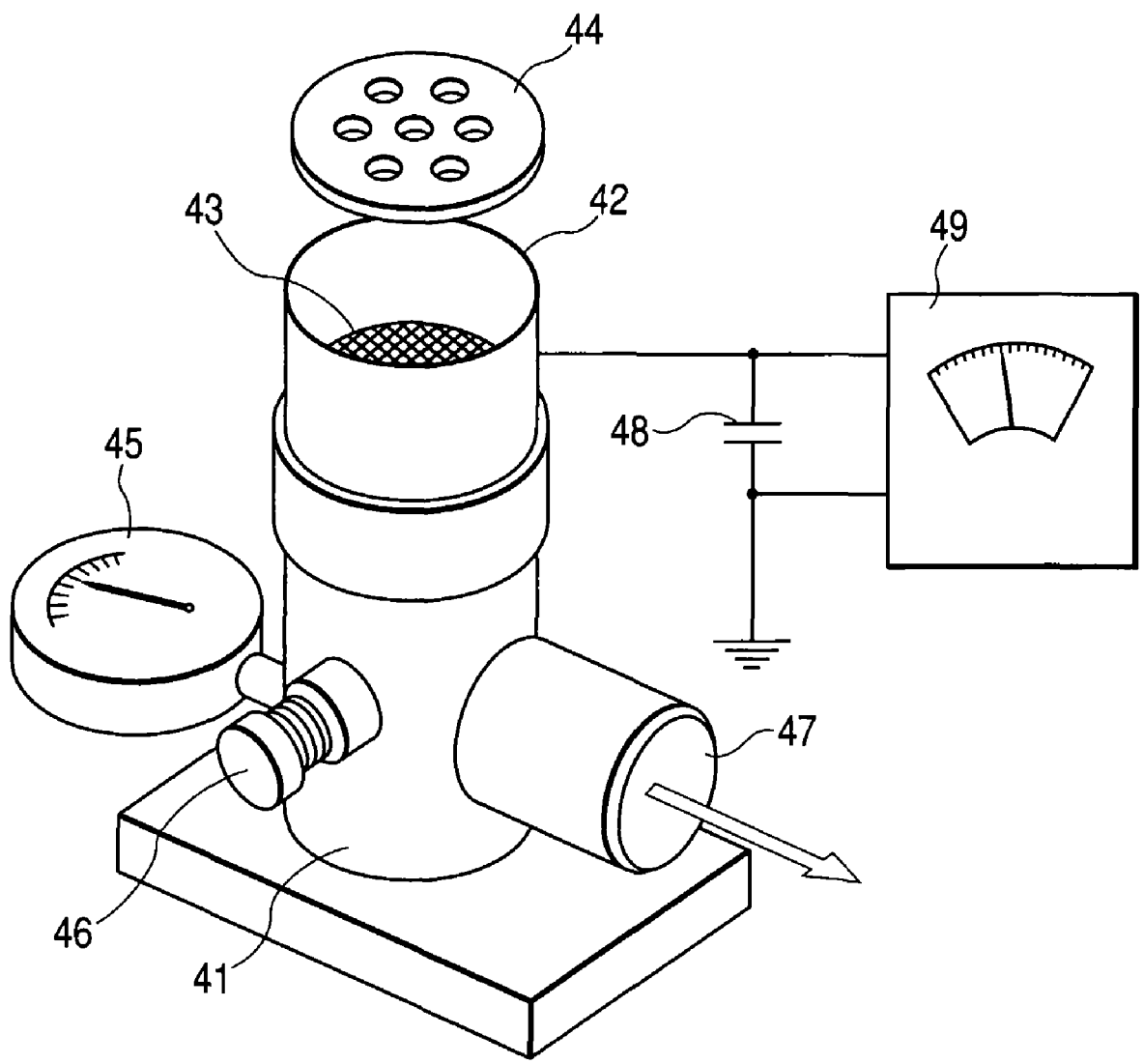
FIG. 5 is a schematic view showing a blow off zone coulometry apparatus for measuring the charge quantity of a toner.

The method of measuring charge quantity by two-component method used in the present invention is shown below. A charge coulometry apparatus shown in FIG. 5 was used for the measurement. At first, a mixture in which 0.5 g of toner, measurement object, is added to 9.5 g of EFV200/300 (manufactured by Powder Tech Corporation) as a carrier is prepared. This mixture is put in a bottle made of polyethylene and of 50 to 100 ml volume and installed on a shaking machine having a constant amplitude in the concussion condition of 100 mm amplitude and 100 times reciprocal movement per one minute and the bottle was shaken for a certain time. Then 1.0 to 1.2 g of the above mixture was placed on a metal measurement container 42 with a screen 43 which is a 500 mesh at the bottom of the charge coulometry apparatus 41 shown in FIG. 5 and covered with a metal lid 44. The mass of the whole measurement container 42 at this time is designated as scale W1 (g). Then it is aspired from aspiration opening 47 by a non-illustrated aspiring machine (at least the parts which contact with the measurement container 42 are insulator) so that the pressure at a vacuum gauge 45 may become 2450 Pa (250 mmAq) by adjusting an air control valve 46. The toner is aspired and removed by aspiring in this state for one minute. The electric potential at an electrometer 49 at this time is designated as V (Volt). Here, numeral 48 denotes a capacitor and the capacity is designated as C (μF). The mass of the whole measurement container at this time is designated as scale W2 (g). The amount of frictional electrification of the toner (μC/g) is calculated from these measured values by the following formula.

Calculation formula: Amount of frictional electrification $(\mu C/g) = C \times V/(W1-W2)$ These operations are performed under a constant environment (for example, it is performed under constant temperature and humidity conditions).

<Molecular Weight Measurement Method and Molecular Weight Distribution of Binder Resin>

A binder resin used for a constitutional material of the toner for developing electrostatic latent images according to the present invention has preferably a peak in a low molecular weight region which is in the range of 3,000 to 15,000 in molecular weight distribution by GPC particularly when prepared by a pulverizing method. That is, when the GPC peaks in a low molecular weight region exceed 15,000, those sufficiently improved of transfer efficiency may be hard to be obtained. When a binder resin having the GPC peaks in a low molecular weight domain at less than 3,000, welding tends to occur at the time of surface treatment and is not preferable.

In the present invention, the molecular weight of a binder resin was measured by GPC (gel permeation chromatography). As a specific measuring method of GPC, the toner is extracted beforehand for 20 hours using a Soxhlet extractor with THF (tetrahydrofuran) solvent and is used as a sample for the measurement. The column was constituted by connecting A-801, 802, 803, 804, 805, 806 and 807 manufactured by Showa Denko and molecular weight distribution was measured with an analytical curve of standard polystyrene resin.

The present inventors have found that the polymer described above has extremely excellent characteristics as a charge control agent. This will be shown in Examples below.

At first, a novel polymer obtained by the present invention and a production process thereof and a novel compound are described by Examples A-1 to R-2. Then utility of the polymers, etc. of the present invention is shown using Examples 1 to 40 and Comparative Examples.

The novel polymer and compound of the present invention and the production processes thereof are not limited to only Examples shown below.

Decision of structures of the obtained compounds is performed in the following experiments. About NMR, $^1$H-NMR (FT-NMR: Bruker DPX400; Resonance frequency: 400 MHz; Measured nuclide: $^1$H, Measured temperature: room temperature).

Furthermore, structure is decided by analyzing it by Fourier transform-infrared absorption (FT-IR) spectrum (Nicolet AVATAR360FT-IR).

$^1$H-NMR measurement was measured with acetone-$d_6$ unless otherwise mentioned in particular.

The average molecular weight of the obtained polymer was estimated by gel permeation chromatography (GPC; Tosoh; column, Polymer Laboratories PLgel 5μ MIXED-C; solvent, DMF/LiBr 0.1% (w/v), polystyrene conversion). As for acid value volumetric determination, potentiometric titration apparatus AT510 (manufactured by Kyoto Electronics Manufacturing) was used.

EXAMPLE A-0

Styrene and 4-vinylbenzoic acid were copolymerized with reference to Macromolecules, 24, 4310-4321 (1991) and Macromolecules, 26, 2791-2795 (1993). As a result, a copolymer which contains a unit shown by the following formula (A-0):

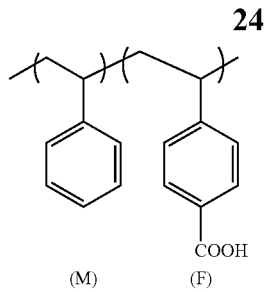

in a content ratio (mol %) of (M):(F)=93:7 was obtained. The average molecular weight of the obtained polymer was number average molecular weight Mn=22,000, weight average molecular weight Mw=52,000.

EXAMPLE A-1

1.5023 g of the polymer obtained in Example A-0, 0.8492 g of 2-aminobenzenesulfonic acid are placed in a three-necked 200 ml flask, added with 56.5 ml of pyridine and stirred under nitrogen atmosphere. Then, 2.57 ml of triphenyl phosphite was added and heated at 120° C. for six hours.

After the reaction ended, pyridine was evaporated, and 150 ml of chloroform was added to dissolve the polymer. The solution was partitioned and washed with 600 ml of 2N hydrochloric acid and, after the solvent was evaporated and 1.2535 g of the polymer was collected. The polymer was dissolved in THF and purified with a permeable membrane using distilled water and isopropanol.

The peak that came from a phenyl group of 2-aminobenzenesulfonic acid was shifted in the result of $^1$H-NMR. As a result, it was confirmed that the obtained polymer was a copolymer which contains a unit shown by the following formula (A-1):

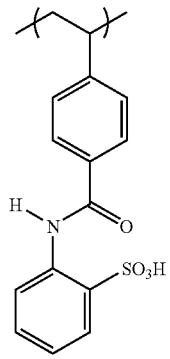

in a content ratio of 6 mol %.

As for the obtained polymer, Mn=20,000, Mw=48,000.

50 g of the polymer was obtained by scale-up and this compound was subjected to toner preparation and estimation as Exemplified Compound A-1.

EXAMPLE A-2

0.9777 g of the polymer obtained in Example A-1 was placed in a 300 mL flask, dissolved with 68.44 ml of chloroform and 17.11 ml of methanol and the mixture was cooled to 0° C. 3.00 ml of 2 mol/L trimethylsilyldiazomethane in hexane solution (product of Aldrich Company) was added as an esterifying agent and the solution was stirred for four hours. After the reaction ended, the solvent was evaporated by an evaporator, and the polymer was collected. Furthermore, 68.44 ml of chloroform and 17.11 ml of methanol were added to dissolve the polymer again and the solvent was evaporated by an evaporator. This operation of re-dissolution and evaporation of the solvent was repeated three times. 0.9552 g of the polymer was obtained by vacuum drying the polymer collected here. The peak of methyl proton as a result of $^1$H-NMR was observed in 3 to 4 ppm. From this, it was confirmed that the obtained polymer was a copolymer which contains a unit shown by the following formula (A-2):

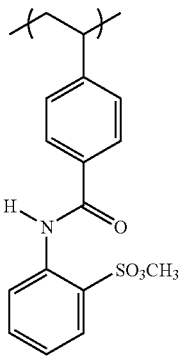

(A-2)

in a content ratio of 6 mol %.

In addition, it became clear that sulfonic acid group was converted to methyl sulfonate group because the equivalence point derived from sulfonic acid was not observed in acid value titration.

As for the obtained polymer, Mn=19,000, Mw=45,000.

50 g of the polymer was obtained by scale-up and this compound was subjected to toner preparation and estimation as Exemplified Compound A-2.

EXAMPLE B-1, EXAMPLE C-1, EXAMPLE D-1, EXAMPLE E-1, EXAMPLE F-1, EXAMPLE G-1

A polymer obtained in Example A-0 was used as a starting material in the same manner as in Example A-1.

Polymers of Examples B-1, C-1, D-1, E-1, F-1 and G-1 were synthesized by performing the same operation as in Example A-1 except for
  Aminosulfonic acid used
  Amount of polymer used
  Amount of aminosulfonic acid used
  Amount of condensing agent used
  Amount of solvent used
as shown in Table 1-1.

The results of synthesis and analysis are shown in Table 1-2.

TABLE 1-1

| Example | Aminosulfonic acid used | Amount of polymer used (g) | Amount of amino-Sulfonic acid used (g) | Amount of condensing agent used (ml) | Amount of solvent used (ml) |
|---|---|---|---|---|---|
| (Reference) A-1 | 2-aminobenzenesulfonic acid | 1.5023 | 0.8492 | 2.57 | 56.50 |
| B-1 | 4-methoxyaniline-2-sulfonic acid | 1.4996 | 1.9894 | 2.57 | 56.50 |
| C-1 | 2-aminobenzenesulfonic acid phenyl ester | 3.0956 | 5.0377 | 5.30 | 113.00 |
| D-1 | 3-aminobenzenesulfonic acid | 2.9954 | 1.6933 | 5.12 | 113.00 |
| E-1 | 4-aminobenzenesulfonic acid | 1.5023 | 1.6985 | 5.14 | 56.50 |
| F-1 | 2-amino-1-naphtalenesulfonic acid | 1.5123 | 1.1020 | 5.17 | 56.50 |
| G-1 | Taurine | 3.0024 | 2.4529 | 10.27 | 113.00 |

TABLE 1-2

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) A-1 | Chemical Formula (A-1) | 6 | 48000 | 20000 | 2.4 | 1.2535 |
| B-1 | Chemical Formula (B-1) | 7 | 47000 | 21000 | 2.2 | 1.3023 |
| C-1 | Chemical Formula (C-1) | 5 | 49000 | 20000 | 2.5 | 2.8842 |
| D-1 | Chemical Formula (D-1) | 5 | 48000 | 20000 | 2.4 | 2.6789 |
| E-1 | Chemical Formula (E-1) | 4 | 47000 | 20000 | 2.4 | 1.2333 |
| F-1 | Chemical Formula (F-1) | 5 | 48000 | 21000 | 2.3 | 1.2256 |
| G-1 | Chemical Formula (G-1) | 3 | 50000 | 19000 | 2.6 | 2.7002 |

*1 Calculated from results of $^1$H-NMR

As for B-1, C-1, D-1 and E-1, since the peak of a phenyl group derived from aminosulfonic acid shifted, introduction of the structure was confirmed and the ratio of the introduced unit was calculated.

As for F-1, since the peak of a naphthyl group derived from aminosulfonic acid shifted, introduction of the structure was confirmed and the ratio of the introduced unit was calculated.

As for G-1, since the peak of an ethylene group derived from aminosulfonic acid shifted, introduction of the structure was confirmed and the ratio of the introduced unit was calculated.

2 Introduced unit structure is shown in Structural Formula 1.

50 g of the polymer was obtained by scale-up and each compound was subjected to toner preparation and estimation as Exemplified Compound B-1, C-1, D-1, E-1, F-1 and G-1.

EXAMPLE B-2, EXAMPLE D-2, EXAMPLE E-2, EXAMPLE F-2, EXAMPLE G-2

Polymers of Examples B-2, C-2, D-2, E-2, F-2 and G-2 were synthesized by performing the same operation as in Example A-2 except for A point that other polymers are used in place of a polymer obtained in A-1 as a starting material Amount of polymer used Amount of esterifying agent used Amount of solvent used as shown in Table 1-3.

The results of synthesis and analysis are shown in Table 1-4.

TABLE 1-3

| Example | Polymer used as starting material | Amount of polymer used (g) | Amount of esterifying agent used (ml) | Amount of chloroform used (ml) | Amount of methanol used (ml) |
| --- | --- | --- | --- | --- | --- |
| (Reference) A-2 | Polymer synthesized in Example A-1 | 0.9777 | 3.00 | 68.44 | 17.11 |
| B-2 | Polymer synthesized in Example B-1 | 1.0825 | 2.91 | 75.78 | 18.94 |
| D-2 | Polymer synthesized in Example D-1 | 1.0023 | 3.04 | 70.16 | 17.54 |
| E-2 | Polymer synthesized in Example E-1 | 0.9950 | 3.09 | 69.65 | 17.41 |
| F-2 | Polymer synthesized in Example F-1 | 1.0236 | 2.98 | 71.65 | 17.91 |
| G-2 | Polymer synthesized in Example G-1 | 1.0056 | 3.17 | 70.39 | 17.60 |

TABLE 1-4

| Example | Introduced unit structure *2 | Ratio of introduced units *1 (mol %) | Molecular weight Mw | Molecular weight Mn | Molecular weight Mw/Mn | Amount of collected polymer (g) |
| --- | --- | --- | --- | --- | --- | --- |
| (Reference) A-2 | Chemical Formula (A-2) | 6 | 45000 | 19000 | 2.4 | 0.9552 |
| B-2 | Chemical Formula (B-2) | 7 | 46000 | 19000 | 2.4 | 0.9332 |
| D-2 | Chemical Formula (D-2) | 5 | 47000 | 19000 | 2.5 | 0.9265 |
| E-2 | Chemical Formula (E-2) | 4 | 45000 | 19000 | 2.4 | 0.9666 |
| F-2 | Chemical Formula (F-2) | 5 | 46000 | 20000 | 2.3 | 0.9335 |
| G-2 | Chemical Formula (G-2) | 3 | 48000 | 18000 | 2.7 | 0.9546 |

*1 Calculated from results of $^1$H-NMR Calculated from the peak derived from aminosulfonic acid ester observed at 3 to 4 ppm.
*2 Introduced unit structure is shown in Structural Formula 1.

50 g of the polymer was obtained by scale-up and each compound was subjected to toner preparation and estimation as Exemplified Compound B-2, D-2, E-2, F-2 and G-2.

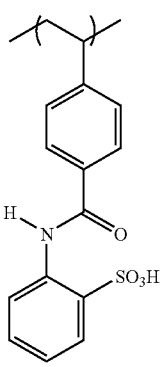 (A-1)
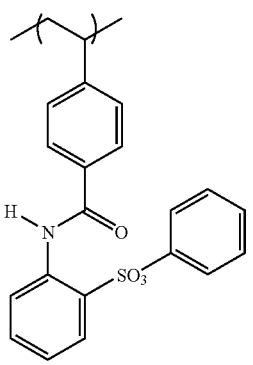 (C-1)
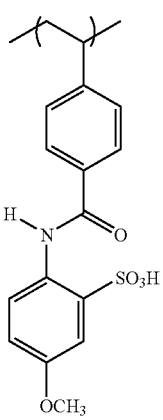 (A-2)
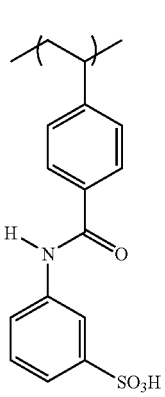 (D-1)
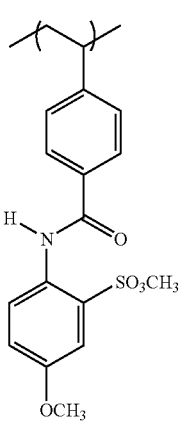 (B-1)
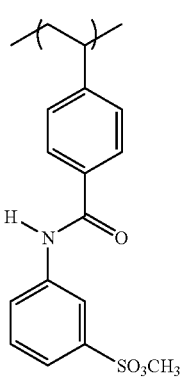 (D-2)
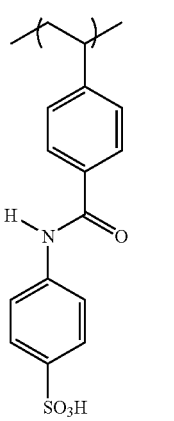 (E1)
(B-2)

(E-2)
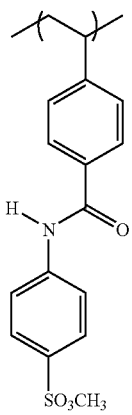

(F-1)
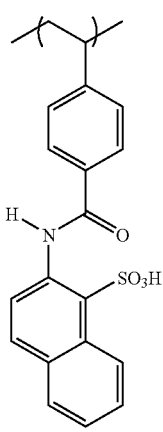

(F-2)
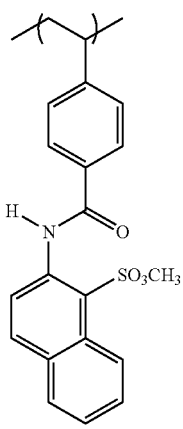

(G-1)
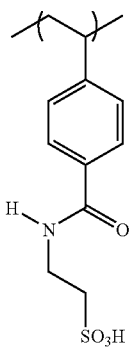

(G-2)
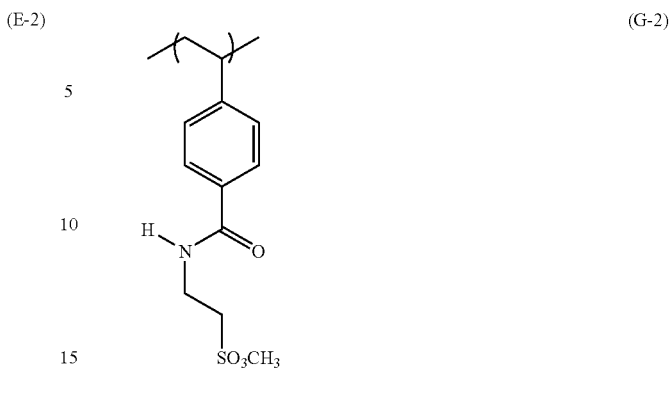

EXAMPLE H-1

Styrene and 4-vinylbenzoic acid were copolymerized according to the same documents as in Example A-1.

As a result, a copolymer which contains a unit shown by the following formula (H-0):

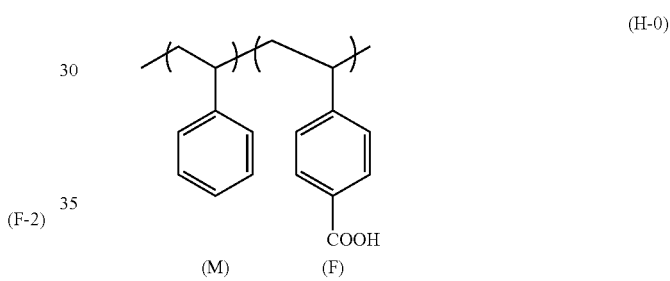
(H-0)

in a content ratio (mol %) of (M):(F)=89:11 was obtained. This was used for the following experiments.

As for the obtained polymer, Mn=25,000, Mw=60,000.

Polymers were synthesized by performing the same operation as in Example A-1 except for Amount of polymer used Amount of aminosulfonic acid used Amount of condensing agent used as shown in Table 2-1.

The results of synthesis and analysis are shown in Table 2-2.

TABLE 2-1

| Example | Amount of polymer used (g) | Amount of aminosulfonic acid used (g) | Amount of condensing agent used (ml) |
|---|---|---|---|
| (Reference) A-1 | 1.5023 | 0.8492 | 2.57 |
| H-1 | 1.5005 | 1.4248 | 4.31 |

TABLE 2-2

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) A-1 | Chemical Formula (A-1) | 6 | 48000 | 20000 | 2.4 | 1.2535 |
| H-1 | Chemical Formula (H-1) | 7 | 58000 | 23000 | 2.5 | 1.1856 |

*1 Calculated from results of $^1$H-NMR Since the peak of a phenyl group derived from aminosulfonic acid shifted, introduction of the structure was confirmed and the ratio of the introduced unit was calculated.
*2 Introduced unit structure is shown in Structural Formula 2.

50 g of the polymer was obtained by scale-up and each compound was subjected to toner preparation and estimation as Exemplified Compound H-1.

EXAMPLE H-2

Polymers were synthesized by performing the same operation as in Example A-2 except for Use of polymer obtained in H-1 in place of the polymer obtained in A-1
  Amount of polymer used
  Amount of esterifying agent used
  Amount of solvent used
as shown in Table 2-3.

The results of synthesis and analysis are shown in Table 2-4.

TABLE 2-3

| Example | Polymer used as starting material | Amount of polymer used (g) | Amount of esterifying agent used (ml) | Amount of chloroform used (ml) | Amount of methanol used (ml) |
|---|---|---|---|---|---|
| (Reference) A-2 | Polymer synthesized in Example A-1 | 0.9777 | 3.00 | 68.44 | 17.11 |
| H-2 | Polymer synthesized in Example H-1 | 0.9990 | 4.80 | 69.93 | 17.48 |

TABLE 2-4

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) | | | | | | |
| A-2 | Chemical Formula (A-2) | 6 | 45000 | 19000 | 2.4 | 0.9552 |
| H-2 | Chemical Formula (H-2) | 6 | 50000 | 28000 | 1.8 | 0.9582 |

*1 Calculated from results of $^1$H-NMR
Calculated from the peak derived from sulfonic acid ester observed at 3 to 4 ppm.
*2 Introduced unit structure is shown in Structural Formula 2.
Structural Formula 2:

TABLE 2-4-continued (H-1) — polymer unit: poly(styrene) with para-benzamide bearing N-H linked to 2-(SO₃H)phenyl (H-2) — polymer unit: poly(styrene) with para-benzamide bearing N-H linked to 2-(SO₃CH₃)phenyl 50 g of the polymer was obtained by scale-up and designated as Exemplified Compound H-2.

EXAMPLE I-0

A copolymer which contains a unit shown by the following formula (I-0C):

(I-0C) — poly(styrene) unit with meta-COOH (F)

in a content ratio of (F)=15 (mol %) was synthesized with reference to Macromolecules, 32, 1453-1462 (1999) and used in the following experiments.

The average molecular weight of the obtained polymer was number average molecular weight Mn=15,000, weight average molecular weight Mw=17,000.

EXAMPLE I-1

After 1.4956 g of the polymer obtained in Example I-0 and 0.8844 g of 2-aminobenzenesulfonic acid were placed in a three-necked 200 ml flask, 113.0 ml of pyridine was added and the mixture was stirred under nitrogen atmosphere, then 2.68 ml of triphenyl phosphite was added, and the mixture was heated at 120° C. for six hours.

After the reaction ended, pyridine was evaporated, and 150 ml of chloroform and 50 ml of methanol were added to dissolve the polymer.

After the solution was partitioned and washed with 150 ml of 2N hydrochloric acid, the solvent of the organic layer was evaporated, and the solution was washed with 100 ml of isopropanol twice, 100 ml of hexane was added and the mixture was washed and filtrated to collect 1.2323 g of the polymer.

The polymer was dissolved in THF and purified with a permeable membrane using distilled water and isopropanol.

The peak that came from a phenyl group of 2-aminobenzenesulfonic acid shifted in the result of $^1$H-NMR. As a result, it was confirmed that the obtained polymer was a copolymer which contains a unit shown by the following formula (I-1):

(I-1) — poly(styrene) unit with meta-benzamide linked via N-H to 2-(SO₃H)phenyl in a content ratio of 12 mol %.

As for the obtained polymer, Mn=13,000, Mw=15,000.

50 g of the polymer was obtained by repeating the preparation method and this compound was subjected to toner preparation and estimation as Exemplified Compound I-1

EXAMPLE I-2

Polymers were synthesized by performing the same operation as in Example A-2 except for Use of polymer obtained in I-1 in place of the polymer obtained in A-1

Amount of polymer used

Amount of esterifying agent used

Amount of solvent used as shown in Table 3-3.

The results are shown in Table 3-4.

TABLE 3-3

| Example | Polymer used as starting material | Amount of polymer used (g) | Amount of esterifying agent used (ml) | Amount of chloroform used (ml) | Amount of methanol used (ml) |
| --- | --- | --- | --- | --- | --- |
| (Reference) A-2 | Polymer synthesized in Example A-1 | 0.9777 | 3.00 | 68.44 | 17.11 |

TABLE 3-3-continued

| Example | Polymer used as starting material | Amount of polymer used (g) | Amount of esterifying agent used (ml) | Amount of chloroform used (ml) | Amount of methanol used (ml) |
|---|---|---|---|---|---|
| I-2 | Polymer synthesized in Example I-1 | 0.9875 | 59.96 | 138.25 | 34.56 |

TABLE 3-4

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) | | | | | | |
| A-2 | Chemical Formula (A-2) | 6 | 45000 | 19000 | 2.4 | 0.9552 |
| I-2 | Chemical Formula (I-2) | 12 | 14000 | 12000 | 1.2 | 0.9324 |

*1 Calculated from results of $^1$H-NMR
Calculated from the peak derived from sulfonic acid ester observed at 3 to 4 ppm.
*2 Introduced unit structure is shown in Structural Formula 3.
Structural Formula 3:

(I-2)

50 g of the polymer was obtained by repeating the preparation method and subjected to toner preparation and estimation as Exemplified Compound I-2.

EXAMPLE J-0

A block copolymer of styrene and 4-vinylbenzoic acid was synthesized with reference to Macromol. Chem. Phys, 195, 3173-3187 (1994) and J. Am. Chem. Soc., 125, 715-728 (2003). As a result, a block copolymer which contains a unit shown by the following formula (J-0):

(J-0)

in which m=210, n=21 was obtained and used in the following experiments.
The average molecular weight of the obtained polymer was Mn=25,000, Mw=30,000.

EXAMPLE L-0

A polymer as a starting material was obtained by copolymerizing styrene and 4-vinylbenzoic acid with reference to Macromolecules, 24, 4310-4321 (1991), Macromolecules, 26, 2791-2795 (1993). The collected polymer was purified with a permeable membrane of molecular cutoff 2000. Then the polymer collected after the dialysis purification was purified with a permeable membrane of molecular cutoff 3500. The polymer was further purified with permeable membranes of molecular cutoff 8000 and 10000 in the same way. As a result, a copolymer which contains a unit shown by the following formula (L-0):

(L-0)

in a content ratio (mol %) of (M):(F)=93:7 was obtained. This was used for the following experiments
As for the obtained polymer, Mn=23,000, Mw=32,000.

EXAMPLE M-0

A polymer as a starting material was obtained by copolymerizing styrene and 4-vinylbenzoic acid with reference to Macromolecules, 24, 4310-4321 (1991) and Macromolecules, 26, 2791-2795 (1993). The collected polymer was purified with a permeable membrane of molecular cutoff 2000. Then the polymer collected after the dialysis purification was purified with a permeable membrane of molecular cutoff 3500. The polymer was further purified with permeable membranes of molecular cutoff 8000 and 10000 in the same way. As a result, a copolymer which contains a unit shown by the following formula (M-0):

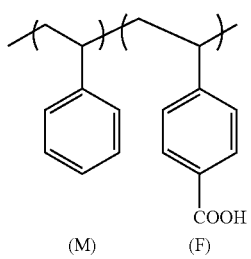

(M-0)

(M) (F)

in a content ratio (mol %) of (M):(F)=88:12 was obtained. This was used for the following experiments.

As for the obtained polymer, Mn=26,000, Mw=36,000.

EXAMPLE J-1, EXAMPLE K-1, EXAMPLE L-1, EXAMPLE M-1

Polymers were synthesized by performing the same operation as in Example A-1 except for Starting polymer material used Aminosulfonic acid used Amount of polymer used Amount of aminosulfonic acid used Amount of condensing agent used Amount of solvent used as shown in Table 4-1.

The results of synthesis and analysis are shown in Table 4-2.

TABLE 4-1

| Example | Polymer used as starting material | Type of Aminosulfonic acid | Amount of polymer used (g) | Amount of aminosulfonic acid used (g) | Amount of condensing agent used (ml) | Amount of solvent used (ml) |
|---|---|---|---|---|---|---|
| (Reference) A-1 | Polymer synthesized in Example A-0 | 2-aminobenzene-sulfonic acid | 1.5023 | 0.8492 | 2.57 | 56.50 |
| J-1 | Polymer synthesized in Example J-0 | 2-aminobenzene-sulfonic acid | 1.5001 | 2.1628 | 6.55 | 56.50 |
| K-1 | Polymer synthesized in Example J-0 | 4-aminobenzene-sulfonic acid | 0.7502 | 1.0816 | 3.27 | 28.25 |
| L-1 | Polymer synthesized in Example L-0 | 2-aminobenzene-sulfonic acid | 1.4998 | 0.8478 | 2.57 | 56.50 |
| M-1 | Polymer synthesized in Example M-0 | 2-aminobenzene-sulfonic acid | 1.5022 | 1.4265 | 4.32 | 56.50 |

TABLE 4-2

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) A-1 | Chemical Formula (A-1) | 6 | 48000 | 20000 | 2.4 | 1.2535 |
| J-1 | Chemical Formula (J-1) | 7 | 29000 | 23000 | 1.3 | 1.2003 |

TABLE 4-2-continued

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| K-1 | Chemical Formula (K-1) | 6 | 29000 | 22000 | 1.3 | 0.6852 |
| L-1 | Chemical Formula (L-1) | 6 | 30000 | 22000 | 1.4 | 1.1563 |
| M-1 | Chemical Formula (M-1) | 9 | 32000 | 23000 | 1.4 | 1.1023 |

*1 Calculated from results of $^1$H-NMR Since the peak of a phenyl group derived from aminosulfonic acid shifted, introduction of the structure was confirmed and the ratio of the introduced unit was calculated.
*2 Introduced unit structure is shown in Structural Formula 4.

50 g of the polymer was obtained by repeating the preparation method and subjected to toner preparation and estimation as Exemplified Compounds J-1, K-1, L-1 and M-1.

EXAMPLE J-2, EXAMPLE K-2, EXAMPLE L-2, EXAMPLE M-2

Polymers were synthesized by performing the same operation as in Example A-2 except for Use of other polymers in place of the polymer obtained in A-1 as a starting material
Amount of polymer used
Amount of esterifying agent used
Amount of solvent used
as shown in Table 4-3.

The results of synthesis and analysis are shown in Table 4-4.

TABLE 4-3

| Example | Polymer used as starting material | Amount of polymer used (g) | Amount of esterifying agent used (ml) | Amount of chloroform used (ml) | Amount of methanol used (ml) |
|---|---|---|---|---|---|
| (Reference) A-2 | Polymer synthesized in Example A-1 | 0.9777 | 3.00 | 68.44 | 17.11 |
| J-1 | Polymer synthesized in Example J-1 | 0.9950 | 3.78 | 69.65 | 17.41 |
| K-1 | Polymer synthesized in Example K-1 | 1.0233 | 3.83 | 71.63 | 17.91 |
| L-1 | Polymer synthesized in Example L-1 | 1.0231 | 3.00 | 71.62 | 17.90 |
| M-1 | Polymer synthesized in Example M-1 | 1.0345 | 4.86 | 72.42 | 18.10 |

TABLE 4-4

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) A-2 | Chemical Formula (A-2) | 6 | 45000 | 19000 | 2.4 | 0.9552 |
| J-1 | Chemical Formula (J-2) | 7 | 28000 | 23000 | 1.2 | 0.9021 |

TABLE 4-4-continued
| K-1 | Chemical Formula (K-2) | 6 | 28000 | 21000 | 1.3 | 0.9124 |
| L-1 | Chemical Formula (L-2) | 6 | 29000 | 21000 | 1.4 | 0.9389 |
| M-1 | Chemical Formula (M-2) | 9 | 31000 | 22000 | 1.4 | 0.9586 |
*1 Calculated from results of $^1$H-NMR
Calculated from the peak derived from sulfonic acid ester observed at 3 to 4 ppm.
*2 Introduced unit structure is shown in Structural Formula 4.
Structural Formula 4:
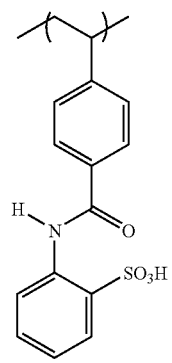
(J-1)
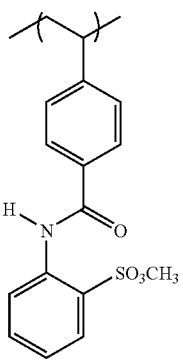
(J-2)
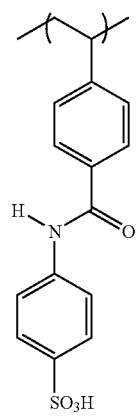
(K-1)
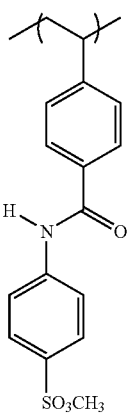
(K-2)
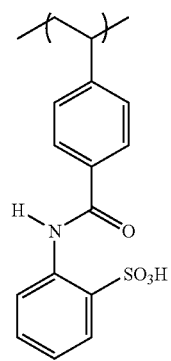
(L-1)
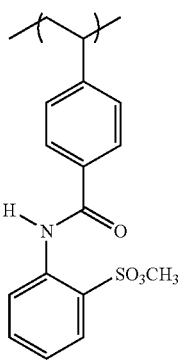
(L-2)

TABLE 4-4-continued

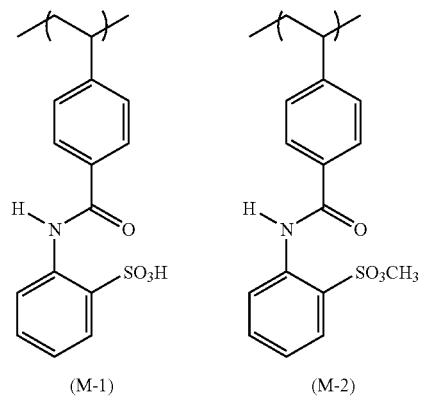

(M-1)   (M-2)

50 g of the polymer was obtained by scale-up and subjected to toner preparation and estimation as Exemplified Compounds J-2, K-2, L-2 and M-2.

EXAMPLE N-0

A monomer represented by Chemical Formula (N-0):

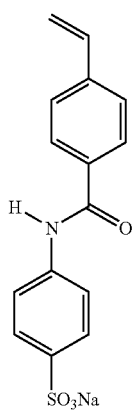

(N-0)

was synthesized with reference to Japanese Patent Application Laid-Open No. 2002-138111 and Macromolecules, 30, 2016-2020 (1997).

50.0 g of 4-aminobenzenesulfonic acid as a starting material was dissolved in 120 ml ion-exchange water. Furthermore, 12.0 g of sodium hydroxide was added thereto and the resultant mixture was heated to 40° C. to be dissolved. After agitation, 100 ml of ion-exchange water was added and then water was evaporated. This operation of re-dissolution in 100 ml of ion-exchange water and evaporation of the solvent was repeated three times.

25.0 ml of distilled water, 24.5 g of sodium hydrogen carbonate and 15.0 ml of methanol were added to this powder and stirred for four hours.

To this, a solution in which 33.3 g of p-vinylbenzoyl chloride was dissolved in 150 ml of THF was added dropwise slowly.

After the dropwise addition was completed, this solution was stirred for 30 minutes and then cooled to 0° C., filtered and crystals were collected. Furthermore, they were washed with methanol and 10.5 g of the monomer was obtained.

The structural determination of the obtained compound was performed by $^1$H-NMR measurement. The obtained monomer here was used for the next polymerization.

EXAMPLE N-1

0.4067 g of the monomer obtained in Example N-0 and 2.7 ml of styrene were put in 30 mL test tube, and added 20 ml of DMSO was added for dissolution and nitrogen bubbling was performed for 12 hours for deaeration.

After 41.2 mg of 2,2'-azobis(isobutyronitrile) dissolved in 5.0 ml of DMSO was added to the test tube as an initiator and the mixture was heated and stirred at 70° C. Nine hours later, the obtained polymer was purified with a permeable membrane, and unreacted monomer and homopolymer of a monomer of Chemical Formula (N-0) were removed by washing it with water and hydrochloric acid, whereby 0.9681 g of the polymer was collected. The peak that came from a phenyl structure of the monomer shifted in the result of $^1$H-NMR. From this, as a result, it was confirmed that the obtained polymer is a copolymer containing a unit represented by the following formula (N-1):

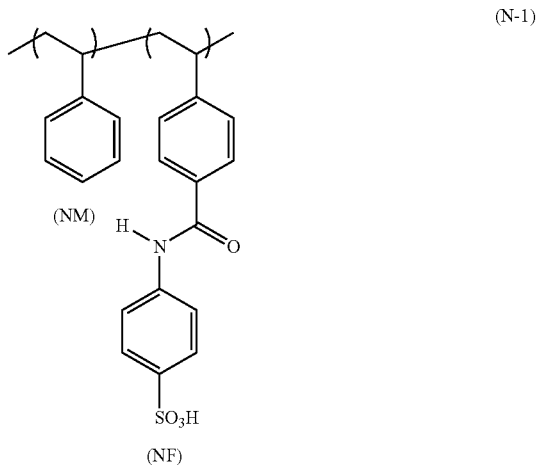

(N-1)

in a content ratio (mol %) of (NM):(NF)=95:5. As for the obtained polymer, Mn=21,000, Mw=36,000. 50 g of the polymer was obtained by scale-up and subjected to toner preparation and estimation as Exemplified Compound N-1.

EXAMPLE N-2

Polymers were synthesized by performing the same operation as in Example A-2 except for
Use of the polymer obtained in N-1 in place of the polymer obtained in A-1 as a starting material
Amount of polymer used
Amount of esterifying agent used
Amount of solvent used
as shown in Table 5-1.

The results of synthesis and analysis are shown in Table 5-2.

TABLE 5-1

| Example | Polymer used as starting material | Amount of polymer used (g) | Amount of esterifying agent used (ml) | Amount of chloroform used (ml) | Amount of methanol used (ml) |
|---|---|---|---|---|---|
| (Reference) A-2 | Polymer synthesized in Example A-1 | 0.9777 | 3.00 | 68.44 | 17.11 |
| N-2 | Polymer synthesized in Example N-1 | 0.9980 | 2.19 | 69.86 | 17.47 |

TABLE 5-2

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) | | | | | | |
| A-2 | Chemical Formula (A-2) | 6 | 45000 | 19000 | 2.4 | 0.9552 |
| N-2 | Chemical Formula (N-2) | 5 | 35000 | 20000 | 1.8 | 0.9325 |

*1 Calculated from results of $^1$H-NMR
Calculated from the peak derived from sulfonic acid ester observed at 3 to 4 ppm.
*2 Introduced unit structure is shown in Structural Formula 5.
Structural Formula 5:

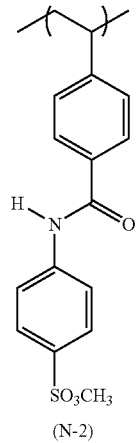

(N-2)

50 g of the polymer was obtained by scale-up and designated as Example Compound N-2.

EXAMPLE O-0

The monomer obtained in Example N-0 was desalted using an ion-exchange resin, and the following (O-0):

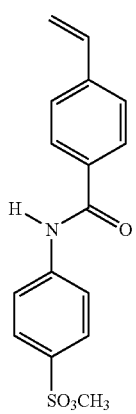

(O-0)

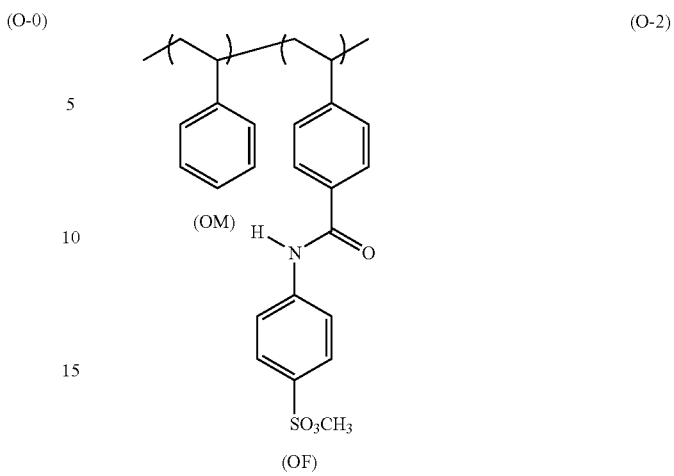

was synthesized with reference to SYNTHETIC COMMUNICATIONS, 15 (12), 21, 1057-1062 (1985).

3.5032 g of desalted compound shown by Chemical Formula (N-0), 20 ml of trimethyl orthoformate and p-benzoquinone as a polymerization inhibitor were placed in a flask and heated at 70° C. under nitrogen atmosphere for five hours. The reaction mixture was cooled and concentrated under reduced pressure. The mixture was washed with 3 L of water twice and 3 L of hexane twice, redissolved in chloroform and dried with anhydrous magnesium sulfate and the solvent was evaporated.

Decision of the structure of the obtained compound was performed with $^1$H-NMR (FT-NMR: Bruker DPX400, Resonance frequency: 400 MHz, Measured nuclide: $^1$H, Used solvent: CDCl$_3$, Measured temperature: room temperature). Because the peak of methyl proton as a result of $^1$H-NMR was observed in 3 to 4 ppm, it was made clear that sulfonic acid group was converted to methyl sulfonate group.

In addition, it was suggested that methyl-esterification proceeded since Na was present in an amount less than detection limit in elemental analysis.

Furthermore, it was made clear that sulfonic acid group was converted to methyl sulfonate group also in that equivalence point which came from sulfonic acid by the acid value titration using potentiometric titration apparatus AT510 (manufactured by Kyoto Electronics Manufacturing) was not observed. This monomer was used for the next polymerization.

EXAMPLE O-2

0.3930 g of the monomer obtained in Example O-0 and 2.7 ml of styrene were put in 30 mL test tube, and added with 20 ml of DMSO to be dissolved, and nitrogen bubbling was performed for 12 hours for deaeration. After 41.2 mg of 2,2'-azobis(isobutyronitrile) dissolved in 5.0 ml of DMSO was added to the test tube, the mixture was heated and stirred at 70° C. Nine hours later, the obtained polymer was purified with a permeable membrane, and unreacted monomer and homopolymer of a monomer of Chemical Formula (O-0) were removed by washing it with water and hydrochloric acid, and 0.9658 g of the polymer was collected. The peak that came from a phenyl structure of the monomer shifted in the result of $^1$H-NMR. From this, as a result, it was confirmed that the obtained polymer is a copolymer containing a unit represented by the following formula (O-2):

in a content ratio (mol %) of (OM):(OF)=95:5. As for the obtained polymer, Mn=20,000, Mw=35,000. 50 g of the polymer was obtained by scale-up and this compound was designated as Exemplified Compound O-1.

EXAMPLE P-2

0.9993 g of the polymer obtained in Example A-1 was put into a flask, 7.30 g of trimethyl orthoformate was added and the mixture was stirred at 80° C. for eight hours.

After the reaction ended, the mixture was added dropwise to 100 ml of hexane and a polymer was collected by filtration. Furthermore, it was dissolved in 10 ml of THF and performed reprecipitation in 100 ml of hexane and 0.8700 g of the polymer was collected.

The peak of methyl proton as a result of $^1$H-NMR was observed in 3 to 4 ppm. From this, it was confirmed that the obtained polymer is a copolymer containing a unit represented by the following formula (P-2):

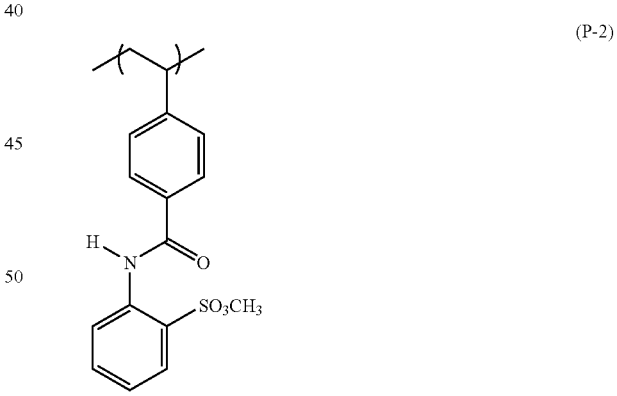

in a content ratio of 6 mol %.

It was clear that sulfonic acid group was converted to methyl sulfonate group since the equivalence point which came from sulfonic acid by the acid value titration was not observed.

As for the obtained polymer, Mn=17,000, Mw=43,000.

EXAMPLE Q-2

1.0032 g of the polymer obtained in Example A-1 was put into a flask, 10.20 g of triethyl orthoformate was added and the mixture was stirred at 100° C. for eight hours.

After the reaction ended, the mixture was added dropwise to 100 ml of hexane and a polymer was collected by filtration. Furthermore, it was dissolved in 10 ml of THF, reprecipitation was performed in 100 ml of hexane and 0.8050 g of the polymer was collected.

From the result of $^1$H-NMR, it was confirmed that the obtained polymer is a copolymer containing a unit represented by the following formula (Q-2):

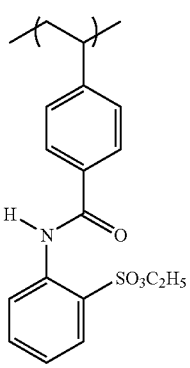

(Q-2)

in a content ratio of 6 mol %.

It was clear that sulfonic acid group was converted to ethyl sulfonate group since the equivalence point which came from sulfonic acid by the acid value titration was not observed.

As for the obtained polymer, Mn=18,000, Mw=46,000.

EXAMPLE R-0

A monomer represented by Chemical Formula (R-0):

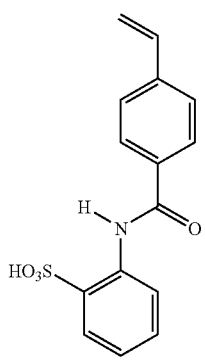

(R-0)

was synthesized with reference to Japanese Patent Application Laid-Open No. 2002-138111 and Macromolecules, 30, 2016-2020 (1997).

6.5 g of 2-aminobenzenesulfonic acid and 8.9 g of triethylamine as starting materials were dissolved in 70 ml of THF, and the mixture was cooled in an ice bath and stirred. To this, p-vinylbenzoyl chloride was added dropwise little by little and after the dropwise addition was completed, the mixture was stirred for five hours. After the reaction ended, 70 ml of ion-exchange water was added and the solvent was evaporated. After the mixture was partitioned and washed with ethyl acetate and 70 ml of 4N hydrochloric acid, the solvent was evaporated, and purification with a silica gel column was performed and 8.0 g of the monomer was obtained.

Decision of the structure of the obtained compound was performed by $^1$H-NMR measurement. The result of the $^1$H-NMR measurement is shown in FIG. 1.

The obtained monomer was used in the next polymerization.

EXAMPLE R-1

303.3 mg of the monomer obtained in Example R-0 and 1.8 ml of styrene were put in a three-necked flask, 45.6 ml of THF was added for dissolution, and nitrogen bubbling was performed for deaeration.

After 32.8 mg of 2,2'-azobis(isobutyronitrile) was added as an initiator, and the mixture was heated and stirred at 70° C. Nine hours later, the obtained polymer was dialyzed with water and isopropanol, and further washed with water and hydrochloric acid, whereby 1.5876 g of the polymer was collected. The peak that came from a double bond of the monomer disappeared and the peak that came from a phenyl structure of the monomer shifted in the result of $^1$H-NMR. From this, as a result, it was confirmed that the obtained polymer is a copolymer containing a unit represented by the following formula (R-1):

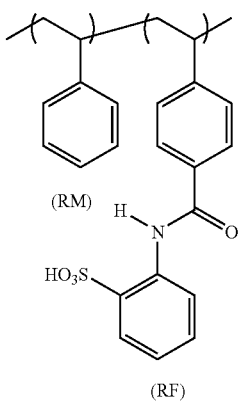

(R-1)

in a content ratio (mol %) of (RM):(RF)=93:7. As for the obtained polymer, Mn=15,000, Mw=28,000.

EXAMPLE R-2

Polymers were synthesized by performing the same operation as in Example A-2 except for Use of the polymer obtained in R-1 in place of the polymer obtained in A-1 as a starting material Amount of polymer used Amount of esterifying agent used Amount of solvent used as shown in Table 6-1.

The results of synthesis and analysis are shown in Table 6-2.

TABLE 6-1

| Example | Polymer used as starting material | Amount of polymer used (g) | Amount of esterification agent used (ml) | Amount of chloroform used (ml) | Amount of methanol used (ml) |
|---|---|---|---|---|---|
| (Reference) A-2 | Polymer synthesized | 0.9777 | 3.00 | 68.44 | 17.11 |

TABLE 6-1-continued

| Example | Polymer used as starting material | Amount of polymer used (g) | Amount of esterification agent used (ml) | Amount of chloroform used (ml) | Amount of methanol used (ml) |
|---|---|---|---|---|---|
| R-2 | in Example A-1 Polymer synthesized in Example R-1 | 0.9878 | 2.96 | 69.20 | 17.30 |

TABLE 6-2

| Example | Introduced unit structure *2 | Ratio of introduced units *1 (mol %) | Molecular weight Mw | Molecular weight Mn | Molecular weight Mw/Mn | Amount of collected polymer (g) |
|---|---|---|---|---|---|---|
| (Reference) | | | | | | |
| A-2 | Chemical Formula (A-2) | 6 | 45000 | 19000 | 2.4 | 0.9552 |
| R-2 | Chemical Formula (R-2) | 6 | 27000 | 160000 | 1.8 | 0.9120 |

*1 Calculated from results of $^1$H-NMR
Calculated from the peak derived from sulfonic acid ester observed at 3 to 4 ppm.
*2 Introduced unit structure is shown in Structural Formula 6.
Structural Formula 6:

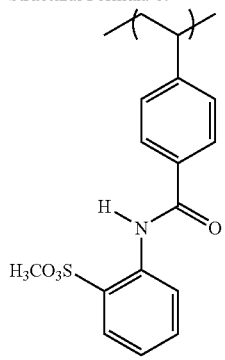

(R-2)

EXAMPLE S-0

Using the monomer obtained in Example R-0, the following (S-0):

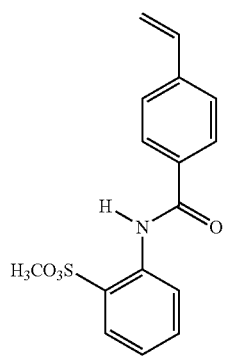

(S-0)

was synthesized.

150 ml of chloroform and 50 ml of methanol were added to 6.0 g of the compound shown by Chemical Formula (R-0) to dissolve under nitrogen atmosphere, and the mixture was cooled to 0° C. in an ice bath. 2 mol/L of trimethylsilyldiazomethane inhexane solution (product of Aldrich Company) was added dropwise little by little, and after the dropwise addition was completed, the mixture was stirred for three hours. After the reaction ended, 300 ml of chloroform and 100 ml of methanol were added for dissolution and the solvent was evaporated. This operation was repeated three times, and purification with a silica gel column was performed and 4.0 g of the monomer was obtained.

Figure 2:
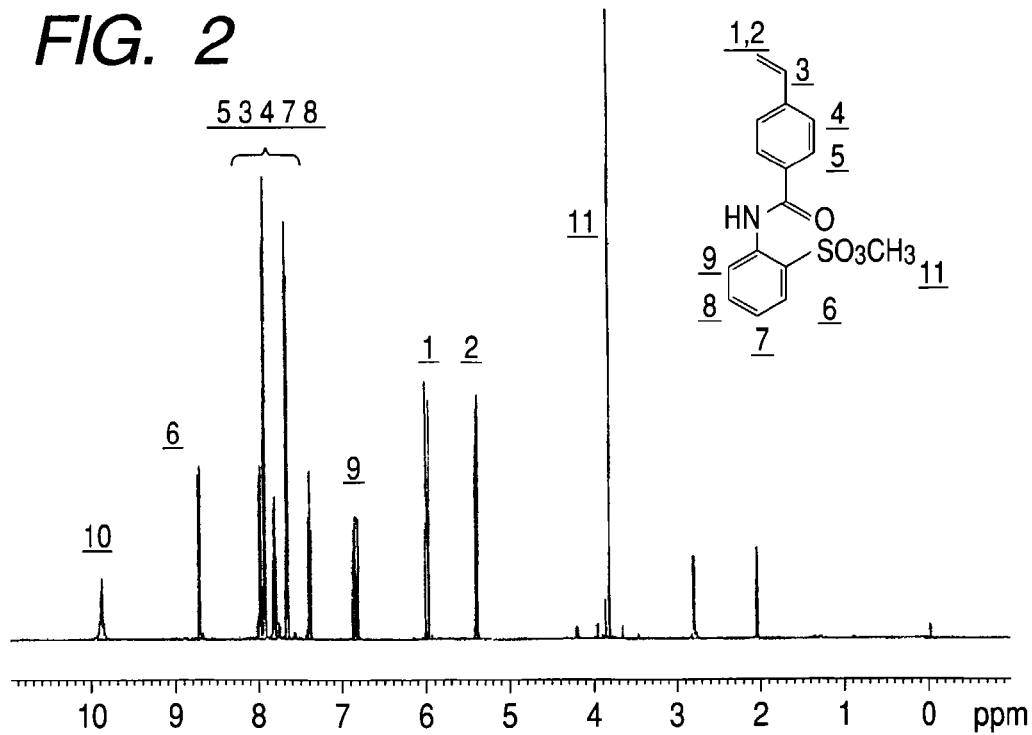
FIG. 2 is a graphical representation showing a measurement result of $^1$H-NMR in Example S-0.

The result of the $^1$H-NMR measurement is shown in FIG. 2.

Since the peak of methyl proton as a result of $^1$H-NMR was observed in 3 to 4 ppm, it was made clear that sulfonic acid group was converted to methyl sulfonate group.

EXAMPLE S-2

317.4 mg of the monomer obtained in Example S-0 and 1.8 ml of styrene were put in a three-necked flask, and 45.9 ml of THF was added for dissolution and nitrogen bubbling was performed for deaeration.

After 32.8 mg of 2,2'-azobis(isobutyronitrile) was added as an initiator and the mixture was heated and stirred at 70° C. Nine hours later, the obtained polymer was dialyzed with water and isopropanol and further washed with water and hydrochloric acid, and 1.7600 g of the polymer was collected. The peak that came from a double bond of the monomer disappeared and the peak that came from a phenyl structure of the monomer shifted in the result of $^1$H-NMR. From this, as a result, it was confirmed that the obtained polymer is a copolymer containing a unit represented by the following formula (R-2):

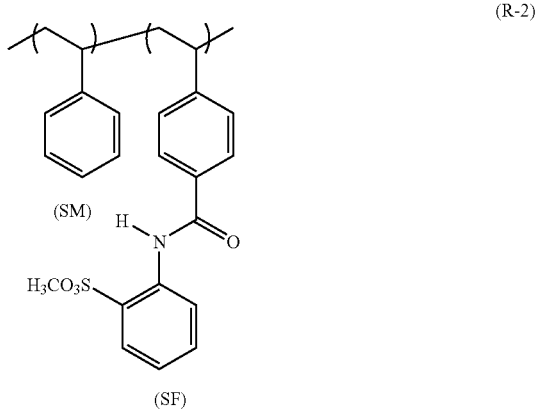

(R-2)

(SM) (SF)

in a content ratio (mol %) of (SM):(SF)=92:8. As for the obtained polymer, Mn=21,000, Mw=34,000.

EXAMPLE T-1

A polymer which contains a unit shown by the following formula (T-0):

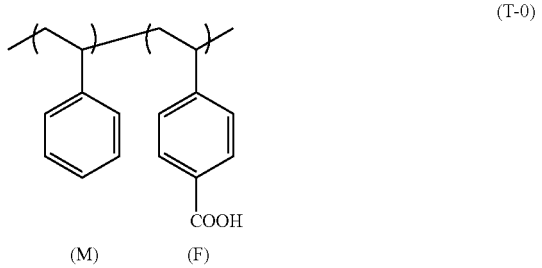

(T-0)

(M) (F)

in a content ratio (mol %) of (M):(F)=91:9 and number average molecular weight Mn=63,000, weight average molecular weight Mw=84,000 was used as a starting material.

After 0.5 g of the polymer, and 0.3597 g of 2-aminobenzenesulfonic acid were placed in a three-necked flask, 4.0 ml of pyridine was added and the mixture was stirred under nitrogen atmosphere, 1.10 ml of triphenyl phosphite was added and the mixture was heated at 115° C. for six hours.

After the reaction ended, pyridine was evaporated and 50 ml of chloroform was added to dissolve the polymer. After the solution was partitioned and washed with 50 ml of 2N hydrochloric acid and 50 ml of water, the solvent was evaporated and the polymer was collected. 0.27 g of the polymer was separated, dissolved in 1.0 ml of chloroform and reprecipitated in 200 ml of isopropanol. The collected polymer was purified with a dialysis membrane.

Figure 3:
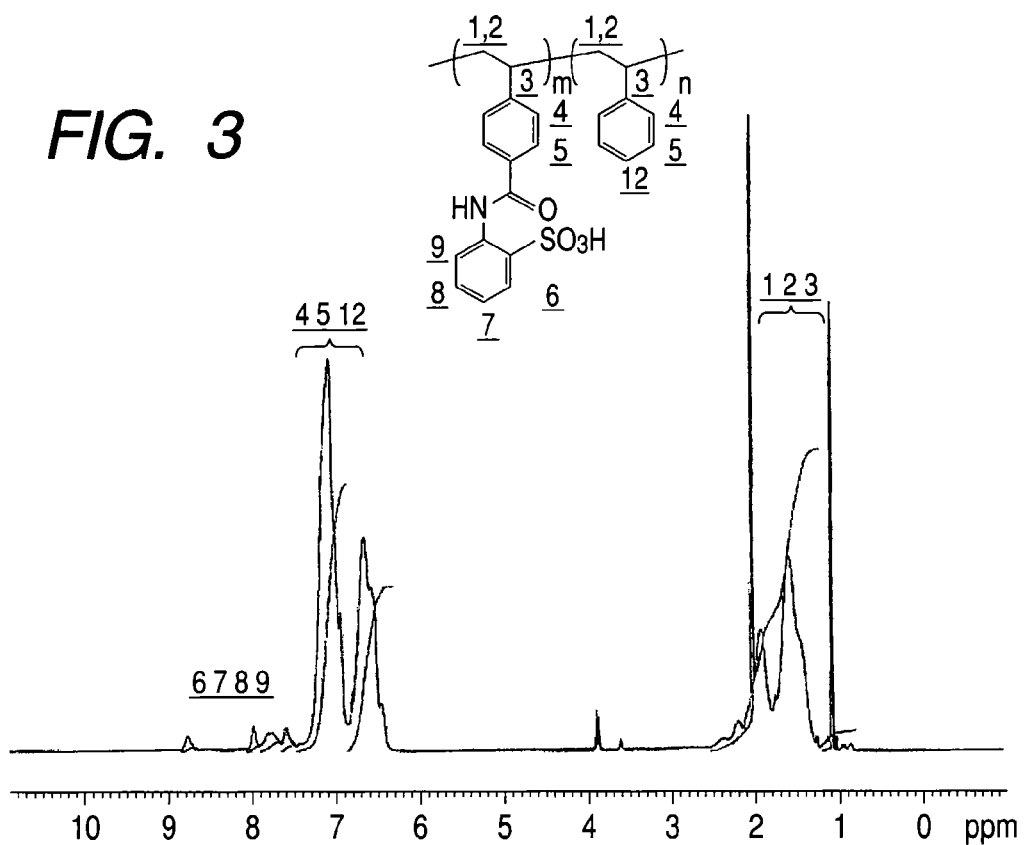
FIG. 3 is a graphical representation showing a measurement result of $^1$H-NMR in Example T-1.

The result of the $^1$H-NMR measurement is shown in FIG. 3.

The peak that came from a double bond disappeared and the peak that came from a phenyl structure of 2-aminobenzenesulfonic acid shifted in the result of $^1$H-NMR. From this, as a result, it was confirmed that the obtained polymer is a copolymer containing a unit represented by the following formula (T-1):

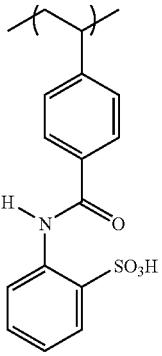

(T-1)

in a content ratio (mol %) of 6 mol %.

EXAMPLE T-2

0.07969 g of the polymer obtained in Example T-1 was placed in an flask, and 2.0 ml of chloroform and 0.5 ml of methanol were added to it to dissolve the polymer and the mixture was cooled to 0° C. 0.3 ml of 2 mol/L of trimethylsilyldiazomethane in hexane solution (product of Aldrich Company) was added as an esterifying agent and the mixture was stirred for four hours. After the reaction ended, the solvent was evaporated by an evaporator and the polymer was collected. Furthermore, 8.0 ml of chloroform and 2.0 ml of methanol were added to dissolve the polymer again and the solvent was evaporated by an evaporator. This operation of re-dissolution and evaporation of the solvent was repeated three times.

0.08339 g of the polymer was obtained by drying the polymer collected here under vacuum.

Figure 4:
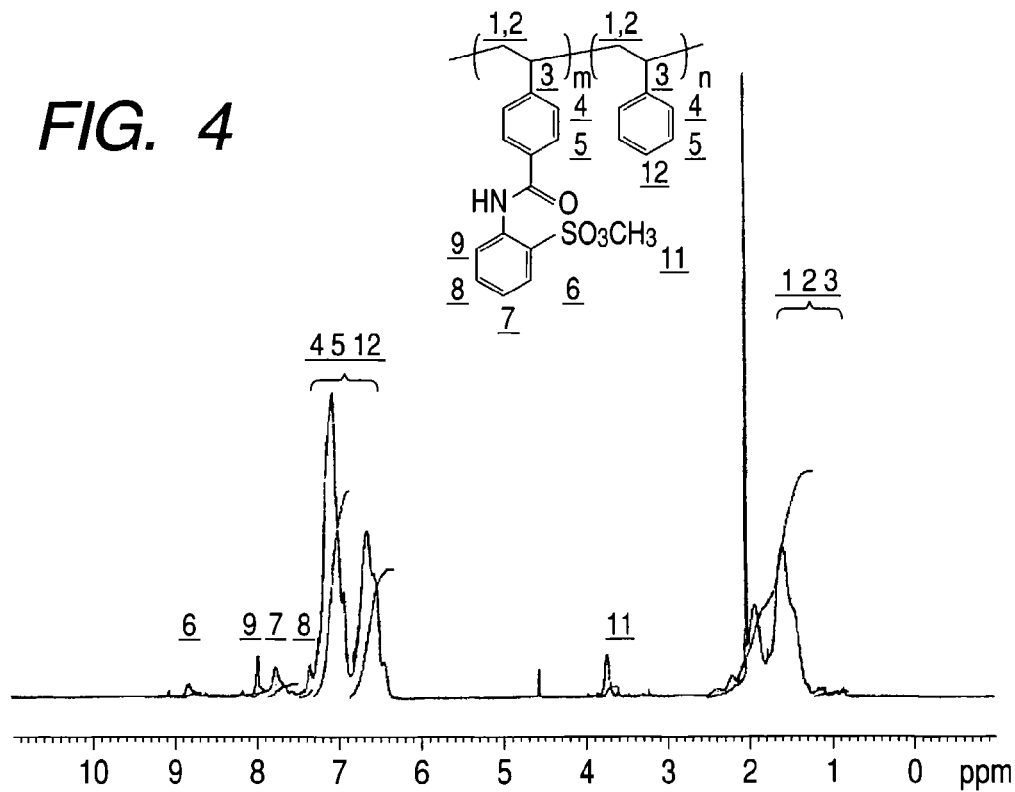
FIG. 4 is a graphical representation showing a measurement result of $^1$H-NMR in Example T-2.

The result of the $^1$H-NMR measurement is shown in FIG. 4.

The peak of methyl proton as a result of $^1$H-NMR was observed in 3 to 4 ppm. From this, it was confirmed that the obtained polymer was a copolymer which contains a unit shown by the following formula (T-2):

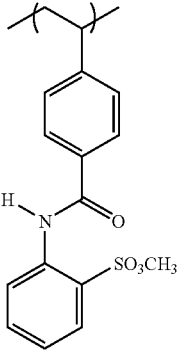

(T-2)

in a content ratio of 6 mol %.

In addition, it became clear that sulfonic acid group was converted to methyl sulfonate group because the equivalence point derived from sulfonic acid was not observed in acid value titration.

As for the obtained polymer, Mn=43,000, Mw=70,000.

EXAMPLE 1

First, $Na_3PO_4$ aqueous solution was added to a four-necked 2 L flask equipped with a high-speed stirrer TK-homomixer, which was adjusted to rotation number of 10,000 rpm and warmed to 60° C. $CaCl_2$ aqueous solution was added slowly to this to prepare an aqueous dispersion containing a poorly water-soluble dispersing agent $Ca_3(PO_4)_2$. In the meantime, the following composition was dispersed with a ballmill for three hours, and 10 parts by mass of 2,2'-azobis(2,4-dimethylvaleronitrile) as a polymerization initiator and 10 parts by mass of a release agent (carnauba wax, melting point 83° C.) were added and a polymerizable monomer composition was prepared.

Styrene monomer: 82 parts by mass
Ethylhexyl acrylate monomer: 18 parts by mass
Divinylbenzene monomer: 0.1 parts by mass
Cyan colorant (C.I. pigment blue 15): 6 parts by mass
Polyethylene oxide resin (Molecular weight 3,200, acid value 8): 5 parts by mass
Exemplified Compound H-2: 2 parts by mass Next, the polymerizable monomer composition obtained above was cast into the aqueous dispersion prepared above and granulated while maintaining a rotation number of 10,000 rpm. Then, while the mixture was stirred with a paddle mixing blade, it was reacted at 65° C. for three hours and then polymerized at 80° C. for six hours and polymerization was finished. After the reaction finished, the suspension was cooled, and after an acid was added to dissolve the slightly water-soluble dispersing agent $Ca_3(PO_4)_2$, the mixture was filtrated, washed with water, and dried to obtain blue polymer particles (1). The size of granulation measured with a Coulter counter multi-sizer (product of Coulter Corporation) of the obtained blue polymerization particles (1) was 7.4 μm in weight average particle size, and the amount of fine powder (existence ratio of particles of 3.17 μm or less in number distribution) was 4.9% in the number of particles.

To 100 parts by mass of the blue polymer particles prepared above, 1.3 parts by mass of fine hydrophobic silica particles (BET: 270 $m^2/g$) treated with hexamethyldisilazane as a flow improver was externally added by dry blending in Henschel mixer. This is designated as blue toner (1) of this Example. Then, 7 parts by mass of this blue toner (1) and 93 parts by mass of a resin coated magnetic ferrite carrier (average particle size: 45 μm) were mixed to prepare a two-component blue developer (1) for the magnetic brush developing.

EXAMPLES 2 TO 5

By using the same method as in Example 1 except that Exemplified Compound H-2 was replaced with Example Compounds B-1, F-1, M-1 and G-2, respectively, blue toners (2) to (5) of Examples 2 to 5 were obtained. The characteristics of these toners were measured in the same manner as in Example 1 and the results are shown in Table 9. Using these, two-component blue developers (2) to (5) of Examples 2 to 5 were also obtained in the same manner as in Example 1.

COMPARATIVE EXAMPLE 1

Blue toner (6) of Comparative Example 1 was obtained in the same manner as in Example 1 except that no Example Compound was used. The characteristics of this toner were measured in the same manner as in Example 1 and the results are shown in Table 7. Using this, two-component blue developer (6) of Comparative Example 1 was also obtained in the same manner as in Example 1.

<Evaluation>

Two-component blue developers (1) to (5) obtained in the above Example 1 and two-component blue developer (6) obtained in Comparative Example 1 were evaluated as follows.

Using the method of measuring the charge quantity as described above, the charge quantity of the toners after stirred for 10 seconds and 300 seconds under respective conditions of normal temperature and normal humidity (25° C., 60% RH) and high temperature and high humidity (30° C., 80% RH). And the measured charge quantity for two-component blow off was rounded off to one decimal place and estimated by the following standard. The results are summarized in Table 7.

[Charging Property]
AA: Very good (−20.0 μC/g or less)
A: Good (more than −20.0 μC/g but −10.0 μC/g or less)
B: Practical use is possible (more than −10.0 μC/g but −5.0 μC/g or less)
C: Practical use is impossible (more than −5.0 μC/g).

EXAMPLES 6 TO 10

By the same method as in Example 1 except that 2.0 parts by mass of Exemplified Compounds B-2, L-1, H-1, J-2 and A-2 were used and a yellow colorant (Hansa yellow G) was used in place of a cyan colorant, yellow toners (1) to (5) of Examples 6 to 10 were obtained. The characteristics of these toners were measured in the same manner as in Example 1 and the results are shown in Table 7. Using these, two-component yellow developers (1) to (5) were also obtained in the same manner as in Example 1.

COMPARATIVE EXAMPLE 2

Yellow toner (6) of Comparative Example 2 was obtained in the same manner as in Example 1 except that no Exemplified Compound was used and a yellow colorant (Hansa yellow G) was used in place of a cyan colorant. The characteristics of this toner were measured in the same manner as in Example 1 and the results are shown in Table 7. Using this, two-component yellow developer (6) of Comparative Example 2 was also obtained in the same manner as in Example 1.

<Evaluation>

The charge quantity of the toner for the two-component yellow developers (1) to (5) obtained in Examples 6 to 10 and the two-component yellow developer (6) obtained in Comparative Example 2 was measured in the same manner as in Example 1 and evaluated. The results are summarized in Table 7.

EXAMPLES 11 TO 15

By the same method as in Example 1 except that 2.0 parts by mass of Exemplified Compounds K-2, C-1, G-1, I-2 and N-1 were used and carbon black (DBP oil absorption amount 110 mL/100 g) was used in place of a cyan colorant, black toners (1) to (5) of Examples 11 to 15 were obtained. The characteristics of these toners were measured in the same manner as in Example 1 and the results are shown in Table 7.

Using these, two-component black developers (1) to (5) were also obtained in the same manner as in Example 1.

COMPARATIVE EXAMPLE 3

The black toner (6) of Comparative Example 3 was obtained in the same manner as in Example 1 except that no Exemplified Compound was used and carbon black (DBP oil absorption 110 mL/100 g) was used in place of a cyan colorant. The characteristics of this toner were measured in the same manner as in Example 1 and the results are shown in Table 7. Using this, two-component black developer (6) of Comparative Example 3 was also obtained in the same manner as in Example 1.

<Evaluation>

The charge quantity of the toner for two-component black developers (1) to (5) obtained in Examples 11 to 15 and two-component black developer (6) obtained in Comparative Example 3 was measured in the same manner as in Example 1 and evaluated. The results are summarized in Table 7.

EXAMPLE 16

Styrene-butyl acrylate copolymer resin (glass transformation temperature 70° C.): 100 parts by mass
Magenta pigment (C.I. pigment red 114): 5 parts by mass
Wax (low molecular polyethylene, melting point 94° C.): 7 parts by mass
Exemplified Compound N-2: 2 parts by mass The above composition was mixed and melt-kneaded in two axis extruder (L/D=30). This blend was roughly crushed in a hammer mill after cooled and finely pulverized in a jet mill, classification was performed and thus magenta pigment particles (1) were obtained by the pulverizing method. The size of granulation of this magenta pigment particle (1) was 7.2 μm in weight average particle size and the amount of fine powder was 5.7% in the number of particles.

To 100 parts by mass of the magenta pigment particles, 1.5 parts by mass of fine hydrophobic silica particles (BET: 250 m$^2$/g) treated with hexamethyldisilazane as a flow improver was added by dry blending in Henschel mixer and magenta (red) toner (1) of this Example was obtained. Then, 7 parts by mass of this magenta (red) toner (1) and 93 parts by mass of a resin coated magnetic ferrite carrier (average particle size: 45 μm) were mixed to prepare a two-component magenta (red) developer (1) for the magnetic brush developing.

EXAMPLES 17 TO 20

By the same method as in Example 16 except that Exemplified Compounds F-2, I-1, K-1 and M-2 were used, magenta (red) toners (2) to (5) of Examples 17 to 20 were obtained. The characteristics of these toners were measured in the same manner as in Example 1 and the results are shown in Table 7. Using these, two-component magenta (red) developers (2) to (5) of Examples 17 to 20 were also obtained in the same manner as in Example 16.

COMPARATIVE EXAMPLE 4

A magenta (red) toner (6) of Comparative Example 4 was obtained in the same manner as in Example 16 except that no Exemplified Compound was used. The characteristics of this toner were measured in the same manner as in Example 1 and the results are shown in Table 7. Using this, a two-component magenta (red) developer (6) of Comparative Example 4 was also obtained in the same manner as in Example 16.

<Evaluation>

The charge quantity of the toner for the two-component magenta (red) developers (1) to (5) obtained in Examples 17 to 20 and the two-component magenta (red) developer (6) obtained in Comparative Example 4 was measured in the same manner as in Example 1 and evaluated. The results are summarized in Table 7.

EXAMPLES 21 TO 25

By the same method as in Example 16 except that 2.0 parts by mass of Exemplified Compounds P-2, D-1, E-2, J-1 and L-2 were used and carbon black (DBP oil absorption amount 110 mL/100 g) was used in place of a magenta pigment, black toners (7) to (11) of Examples 21 to 25 were obtained. The characteristics of these toners were measured in the same manner as in Example 1 and the results are shown in Table 7. Using these, the two-component black developers (7) to (11) were also obtained in the same manner as in Example 16.

COMPARATIVE EXAMPLE 5

A black toner (12) of Comparative Example 5 was obtained in the same manner as in Example 16 except that no Exemplified Compound was used and carbon black (DBP oil absorption amount 110 mL/100 g) was used in place of a magenta pigment. The characteristics of this toner were measured in the same manner as in Example 1 and the results are shown in Table 7. Using this, a two-component black developer (12) of Comparative Example 5 was also obtained in the same manner as in Example 16.

<Evaluation>

The charge quantity of the toner for the two-component black developers (7) to (11) obtained in Examples 21 to 25 and the two-component black developer (12) obtained in Comparative Example 5 was measured in the same manner as in Example 1 and evaluated. The results are summarized in Table 7.

EXAMPLE 26

Polyester resin: 100 parts by mass
Carbon black (DBP oil absorption amount 110 mL/100 g): 5 parts by mass
Wax (low molecular polyethylene, melting point 94° C.): 7 parts by mass
Exemplified Compound E-1: 2 parts by mass A polyester resin was synthesized as follows. 751 parts of bisphenol A propylene oxide 2 mol adduct, 104 parts of terephthalic acid and 167 parts of anhydrous trimellitic acid were polycondensed using 2 parts of dibutyl tin oxide as a catalyst, and a polyester resin having a softening point of 125° C. was obtained.

The above composition was mixed and melt-kneaded in two axis extruder (L/D=30). This blend was roughly crushed in a hammer mill after cooled and finely pulverized in jet mill, classification was performed and thus black colorant particles (13) were obtained by pulverizing method. The particle size of these black colorant particles (13) was 7.6 μm in weight average particle size and the amount of fine powder was 4.8% in the number of particles.

To 100 parts by mass of the black colorant particles (13), 1.5 parts by mass of fine hydrophobic silica particles (BET: 250 m$^2$/g) treated with hexamethyldisilazane as flow improver was added by dry blending in Henschel mixer, and black toner (13) of this Example was obtained. Then, 7 parts by mass of the obtained black toner (13) and 93 parts by mass of a resin coated magnetic ferrite carrier (average particle size: 45 μm) were mixed to prepare a two-component black developer (13) for the magnetic brush developing.

EXAMPLES 27 TO 30

Black toners (14) to (17) of Examples 27 to 30 were obtained by the same method as in Example 26 except that Exemplified Compound E-1 was replaced with Exemplified Compounds A-1, D-2, Q-2 and O-2, respectively. The characteristics of these toners were measured in the same manner as in Example 1 and the results are shown in Table 7. Using these, two-component black developers (14) to (17) of Examples 27 to 30 were also obtained in the same manner as in Example 26.

COMPARATIVE EXAMPLE 6

A black toner (18) of Comparative Example 6 was obtained in the same manner as in Example 26 except that no Exemplified Compound was used. The characteristics of this toner were measured in the same manner as in Example 1 and the results are shown in Table 7. Using this, a two-component black developer (18) of Comparative Example 6 was also obtained in the same manner as in Example 26.

<Evaluation>

The charge quantity of the toner for the two-component black developers (13) to (17) obtained in Examples 26 to 30 and the two-component black developer (18) obtained in Comparative Example 6 was measured in the same manner as in Example 1 and evaluated. The results are summarized in Table 7.

TABLE 7

| | | | Particle size distribution | | Charging property | | | |
| | | | | | Normal temperature and normal humidity (Q/M) | | High temperature and high humidity (Q/M) | |
| Example | No. of Exemplified Compound | No. of toner | Average particle size (μm) | Amount of fine powder (%) | 10 seconds | 300 seconds | 10 seconds | 300 seconds |
|---|---|---|---|---|---|---|---|---|
| 1 | H-2 | Blue 1 | 7.4 | 4.9 | AA | AA | AA | AA |
| 2 | B-1 | Blue 2 | 7.5 | 5.5 | AA | AA | AA | AA |
| 3 | F-1 | Blue 3 | 6.8 | 5.1 | AA | AA | AA | AA |
| 4 | M-1 | Blue 4 | 7.2 | 5.3 | AA | AA | AA | AA |
| 5 | G-2 | Blue 5 | 7.2 | 5.5 | AA | AA | AA | AA |
| 6 | B-2 | Yellow 1 | 7.3 | 5.1 | AA | AA | AA | AA |
| 7 | L-1 | Yellow 2 | 7.1 | 5.3 | AA | AA | AA | AA |
| 8 | H-1 | Yellow 3 | 7.0 | 5.2 | AA | AA | AA | AA |
| 9 | J-2 | Yellow 4 | 7.2 | 4.9 | AA | AA | AA | AA |
| 10 | A-2 | Yellow 5 | 7.2 | 5.0 | AA | AA | AA | AA |
| 11 | K-2 | Black 1 | 7.1 | 5.0 | AA | AA | AA | AA |
| 12 | C-1 | Black 2 | 7.3 | 5.5 | AA | AA | AA | AA |
| 13 | G-1 | Black 3 | 7.1 | 5.0 | AA | AA | AA | AA |
| 14 | I-2 | Black 4 | 7.3 | 5.1 | AA | AA | AA | AA |
| 15 | N-1 | Black 5 | 7.0 | 5.1 | AA | AA | AA | AA |
| 16 | N-2 | Red 1 | 7.2 | 5.7 | AA | AA | AA | AA |
| 17 | F-2 | Red 2 | 7.0 | 5.3 | AA | AA | AA | AA |
| 18 | I-1 | Red 3 | 7.0 | 5.2 | AA | AA | AA | AA |
| 19 | K-1 | Red 4 | 7.2 | 5.8 | AA | AA | AA | AA |
| 20 | M-2 | Red 5 | 7.1 | 5.5 | AA | AA | AA | AA |
| 21 | P-2 | Black 7 | 7.3 | 4.9 | AA | AA | AA | AA |
| 22 | D-1 | Black 8 | 7.5 | 5.7 | AA | AA | AA | AA |
| 23 | E-2 | Black 9 | 7.0 | 5.3 | AA | AA | AA | AA |
| 24 | J-1 | Black 10 | 7.4 | 5.4 | AA | AA | AA | AA |
| 25 | L-2 | Black 11 | 7.0 | 5.4 | AA | AA | AA | AA |
| 26 | E-1 | Black 13 | 7.6 | 4.8 | AA | AA | AA | AA |
| 27 | A-1 | Black 14 | 7.1 | 5.7 | AA | AA | AA | AA |
| 28 | D-2 | Black 15 | 7.2 | 5.6 | AA | AA | AA | AA |
| 29 | Q-2 | Black 16 | 7.4 | 5.3 | AA | AA | AA | AA |
| 30 | O-2 | Black 17 | 7.3 | 5.2 | AA | AA | AA | AA |
| Comparative Ex. 1 | — | Blue 6 | 7.1 | 5.2 | C | C | C | C |
| Comparative Ex. 2 | — | Yellow 6 | 7.3 | 5.4 | C | C | C | C |
| Comparative Ex. 3 | — | Black 6 | 7.1 | 5.1 | C | B | C | B |
| Comparative Ex. 4 | — | Red 6 | 7.5 | 5.6 | C | B | C | B |
| Comparative Ex. 5 | — | Black 12 | 7.6 | 5.7 | C | B | C | C |
| Comparative Ex. 6 | — | Black 18 | 7.6 | 4.9 | C | B | C | B |

(For the sake of simplicity, magenta is referred to as red)

EXAMPLES 31 TO 36 AND COMPARATIVE EXAMPLES 7 TO 12

LBP5500 (manufactured by Canon Inc.) was remodeled and used for evaluation in Example 31 to Example 36 and Comparative Example 7 to Comparative Example 12.

In these tests, toner images were formed by cyan toner, yellow toner, magenta toner or black toner obtained in Examples 1, 6, 11, 16, 21 and 26 and Comparative Examples 1 to 6 as a developer.

<Evaluation>

Printing was performed by remodeling LBP5500 so that the printing rate was 8 sheets (A4 size)/minute under the above-mentioned condition and normal temperature and normal humidity (25° C., 60% RH) and high temperature and high humidity (30° C., 80% RH).

A printout test was performed on a monochromatic intermittent mode by respectively using and supplying one by one the toners of Examples 1, 6, 11, 16, 21 and 26 and the toners of Comparative Examples 1 to 6. The obtained printout images were evaluated with regard to the following items. The results of evaluation were summarized in Table 8. Here, the intermittent mode is a mode in which the developing device is paused for 10 seconds every time a sheet is printed out to accelerate deterioration of the toner by preliminary operation at the time of reboot.

[Printout Image Evaluation]

1. Image Density

Printout was performed on common plain copying paper (75 g/m$^2$) for the predetermined number of sheets and evaluation was performed based on the degree of density maintained at the last printout image as compared to the initial image. Here, the density of image was measured using Macbeth reflection densitometer (manufactured by Macbeth Corporation), and the relative density against the printout image of a white area where the density on the original is 0.00 was measured and used for evaluation.

AA: Excellent (Image density at the last printout is 1.40 or more)
A: Good (Image density at the last printout is 1.35 or more but less than 1.40)
B: Acceptable (Image density at the last printout is 1.00 or more but less than 1.35)
C: Unacceptable (Image density at the last printout is less than 1.00)

2. Image Fog

Printout was performed on common plain copying paper (75 g/m$^2$) for predetermined number of sheets and evaluation was performed based on the whole white image at the last printout. Specifically, evaluation was conducted by the following method. Measurement was conducted with a reflection densitometer (REFLECTOMETER MODEL TC-6DS manufactured by TOKYO DENSHOKU CO., LTD). That is, the lowest value of the reflection density on the whole white area after printing was determined as Ds, the average value of the reflection density of the paper before printing was determined as Dr and (Ds−Dr) was determined from these values and this is assumed as fog amount and evaluated by the following standard.

AA: Excellent (fog amount is 0% or more but less than 1.5%)
A: Good (fog amount is 1.5% or more but less than 3.0%)
B: Practically usable (fog amount is 3.0% or more but less than 5.0%)
C: Practically unusable (fog amount is 5.0% or more)

3. Transfer Property

Printout was performed on common plain copying paper (75 g/m$^2$) for predetermined number of sheets using whole black image and evaluation was performed by visually observing the blank amount of the image at the last printout image and evaluated by the following standard.

AA: Excellent (almost no blank occurred)
A: Good (slight)
B: Practically usable
C: Practically unusable In addition, flaws on the surface of the photoconductive drum or intermediate transfer member, occurrence of retention of the remaining toner and the effect on the printout image (matching with LBP5500) after image output was conducted till 5,000 sheets were visually evaluated in Example 31 to Example 36 and Comparative Example 7 to Comparative Example 12.

There were no flaws on the surface of the photoconductive drum or intermediate transfer member, occurrence of retention of the remaining toner observed and matching with LBP5500 was excellent in the system using the toner of Example 31 to Example 36. On the other hand, retention of the toner on the photoconductive drum was recognized in any system using the toners of Comparative Example 7 to Comparative Example 12. Furthermore, retention of the toner and surface flaws were recognized on the intermediate transfer member and defects also occurred on the image in the form of longitudinal lines and thus caused problems in matching with LBP5500 in the system using the toners of Comparative Example 7 to Comparative Example 12.

TABLE 8

| Example | No. of toner | Normal temperature and normal humidity | | | High temperature and high humidity | | |
|---|---|---|---|---|---|---|---|
| | | Image density | Image fog | Transfer Property | Image density | Image fog | Transfer Property |
| 31 | Blue 1 | AA | AA | AA | AA | AA | AA |
| 32 | Yellow 1 | AA | AA | AA | AA | AA | AA |
| 33 | Black 1 | AA | AA | AA | AA | AA | AA |
| 34 | Red 1 | AA | AA | AA | AA | AA | AA |
| 35 | Black 7 | AA | AA | AA | AA | AA | AA |
| 36 | Black 13 | AA | AA | AA | AA | AA | AA |
| Compar. Ex. 7 | Blue 6 | C | C | C | C | C | C |
| Compar. Ex. 8 | Yellow 6 | C | C | C | C | C | C |
| Compar. Ex. 9 | Black 6 | B | B | C | B | C | C |
| Compar. Ex. 10 | Red 6 | B | B | C | B | C | C |
| Compar. Ex. 11 | Black 12 | B | B | C | C | C | C |
| Compar. Ex. 12 | Black 18 | B | B | C | B | C | C |

EXAMPLES 37 TO 39 AND COMPARATIVE EXAMPLES 13 TO 15

When carrying out Examples 37 to 39 and Comparative Examples 13 to 15, the toners obtained in Examples 1, 6 and 11 and Comparative Examples 1 to 3 were used as a developer, respectively. LBP5500 was remodeled by equipping reuse mechanism (system using collected toners) as means to form an image and thus reset image forming apparatus was used.

As above, printout was performed to 30,000 sheets under normal temperature and normal humidity (25° C., 60% RH) on consecutive mode by sequentially supplying the toner at a printing rate of 8 sheets (A4 size)/minute.

Here, the consecutive mode is a mode in which the developing device is not posed and the consumption of toner is promoted.

Image density was measured on the obtained printout image and the durability thereof was evaluated in the following standard. In addition, the image on the 10,000th sheet was observed and the image fog was evaluated in the following standard. At the same time, the state of each device which constituted LBP5500 was observed after an durability test and matching between each device and each of the above toners was also evaluated. The results of these are summarized in Table 9.

[Change in Image Density at the Time of Durability Test]

Printout was performed on common plain copying paper (75 g/m$^2$) for the predetermined number of sheets and evaluation was performed based on the degree of density maintained at the last printout image as compared to the initial image. Here, the density of the image was measured using Macbeth reflection densitometer (manufactured by Macbeth Corporation), and the relative density against the printout image of a white area where the density on the original is 0.00 was measured and used for evaluation.

AA: Excellent (Image density at the last printout is not less than 1.40)
A: Good (Image density at the last printout is 1.35 or more but less than 1.40)
B: Acceptable (Image density at the last printout is 1.00 or more but less than 1.35)
C: Unacceptable (Image density at the last printout is less than 1.00)

[Image Fog]

Printout was performed on common plain copying paper (75 g/m$^2$) for the predetermined number of sheets and evaluation was performed at the last printout based on the whole white image. Evaluation was conducted by the method using a reflection densitometer (REFLECTOMETER MODEL TC-6DS manufactured by TOKYO DENSHOKU CO., LTD).

[Image Forming Apparatus Matching Evaluation]

1. Matching with Developing Sleeve

After the printout test ended, the state of retention of the remaining toner onto the surface of the developing sleeve and influence on the printout image was visually evaluated.
AA: Excellent (Not occurred)
A: Good (Almost not occurred)
B: Practically usable (There is retention, but there is little influence on the image)
C: Practically unusable (A lot of retention and an uneven image occurred)

2. Matching with Photoconductive Drum

Flaws on the photoconductive drum, occurrence of retention of the remaining toner and the effect on the printout image were visually evaluated.
AA: Excellent (Not occurred)
A: Good (Flaws slightly observed but no effect on the image)
B: Practically usable (There is retention and flaws but there is little influence on the image)
C: Practically unusable (A lot of retention and defects in the image in the form of longitudinal lines occurred)

3. Matching with Fixing Equipment

The surface of the fixation film was observed and averaged with the results of surface quality and retention of remaining toner and the durability was evaluated.

(1) Surface Quality

Flaws or scratches on the surface of the fixation film was visually observed after the printout test and evaluated.
AA: Excellent (not occurred)
A: Good (almost not occurred)
B: Practically usable
C: Practically unusable (2) State of Retention of Remaining Toner The state of retention of the remaining toner on the surface of the fixation film was visually observed and evaluated after the printout test ended.
AA: Excellent (not occurred)
A: Good (almost not occurred)
B: Practically usable
C: Practically unusable

TABLE 9

| | | Evaluation of printout image | | | | | Matching with image forming apparatus | | | |
| | | Change in image density at the time of durability test | | | | Image fog | | Photo- | Fixing equipment | |
| | Toner | Initial state | 1000 sheets | 10000 sheets | 30000 sheets | (10000 sheets) | Developing sleeve | conductive drum | Surface quality | Retention of toner |
|---|---|---|---|---|---|---|---|---|---|---|
| Example | | | | | | | | | | |
| 37 | Blue 1 | AA | AA | AA | AA | AA | AA | AA | AA | AA |
| 38 | Yellow 1 | AA | AA | AA | AA | AA | AA | AA | AA | AA |
| 39 | Black 1 | AA | AA | AA | AA | AA | AA | AA | AA | AA |
| Comparative Example | | | | | | | | | | |
| 13 | Blue 6 | B | C | C | C | C | C | C | C | C |
| 14 | Yellow 6 | B | C | C | C | C | C | C | C | C |
| 15 | Black 6 | A | B | C | C | C | C | C | C | C |

EXAMPLE 40

The toner reuse mechanism of LBP5500 used in Examples 37 to 39 and Comparative Examples 13 to 15 was removed and the printout speed was changed to 16 sheets (A4 size)/minute. The other conditions were the same as in Example 37, and a printout test was performed on a consecutive mode by sequentially supplying the blue toner (1) of Example 1.

Here, the consecutive mode is a mode in which the developing device is not posed and the consumption of toner is promoted.

Obtained printout images and matching with LBP5500 used were evaluated for the same items as in Examples 37 to 39 and Comparative Examples 13 to 15. As a result, good results were obtained in every item.

The polymer of the present invention can be applied, for example, to a charge control agent contained in a toner used for electronograph technology.

This application claims priority from Japanese Patent Application No. 2005-328179 filed Nov. 11, 2005, which is hereby incorporated by reference herein in its entirety.

The invention claimed is:

1. A polymer having a unit represented by Chemical Formula (1):

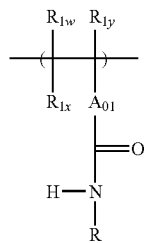

(1)

wherein R represents -$A_1$-$SO_2R_1$; $R_{1w}$, and $R_{1x}$ are each independently a halogen atom or a hydrogen atom; $R_{1y}$ is a $CH_3$ group, a halogen atom or a hydrogen atom; $A_{01}$ is a substituted or unsubstituted aromatic ring structure or a substituted or unsubstituted heterocyclic structure; $A_1$ is a substituted or unsubstituted aliphatic hydrocarbon structure, a substituted or unsubstituted benezene ring structure, a substituted or unsubstituted naphthalene ring structure, or a substituted or unsubstituted heterocyclic structure; $R_1$ is OH, a halogen atom, ONa, OK or $OR_{1a}$; $R_{1a}$ is a substituted or unsubstituted aliphatic hydrocarbon structure, a substituted or unsubstituted aromatic ring structure or a substituted or unsubstituted heterocyclic structure.

2. A polymer which is a copolymer of a unit according to claim 1 and a unit derived from a vinyl-based monomer represented by Chemical Formula (101):

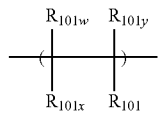

(101)

wherein $R_{101w}$ and $R_{101x}$ are each independently a halogen atom or a hydrogen atom;

$R_{101y}$ is a $CH_3$ group, a halogen atom or a hydrogen atom; $R_{101}$ is any one of a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{101a}$, —O—$R_{101b}$, —COO—$R_{101c}$, —OCO—$R_{101d}$, —CONR$_{101e}$R$_{101f}$, —CN or a ring structure containing an N atom; $R_{101a}$, $R_{101b}$, $R_{101c}$, $R_{101d}$, $R_{101e}$ and $R_{101f}$ are each independently a hydrogen atom, a substituted or unsubstituted aliphatic hydrocarbon structure, a substituted or unsubstituted aromatic ring structure or a substituted or unsubstituted heterocyclic structure.

3. A compound represented by Chemical Formula (201):

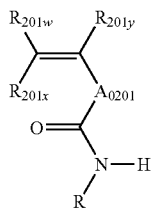

(201)

wherein R represents -$A_{201}$-$SO_2R_{201}$; $R_{201w}$ and $R_{201x}$ are each independently a halogen atom or a hydrogen atom; $R_{201y}$ is a $CH_3$ group, a halogen atom or a hydrogen atom;

$A_{0201}$ is a substituted or unsubstituted aromatic ring structure or a substituted or unsubstituted heterocyclic structure;

$A_{201}$ is a substituted or unsubstituted aliphatic hydrocarbon structure, a substituted or unsubstituted benzene ring structure, a substituted or unsubstituted naphthalene ring structure, or a substituted or unsubstituted heterocyclic structure;

$R_{201}$ is OH, a halogen atom, ONa, OK or $OR_{201a}$; $R_{201a}$ is a substituted or unsubstituted aliphatic hydrocarbon structure, a substituted or unsubstituted aromatic ring structure or a substituted or unsubstituted heterocyclic structure.

4. A toner for developing an electrostatic latent image, comprising a binder resin, a colorant, and a polymer according to claim 1.

* * * * *